United States Patent [19]

Sheppard

[11] Patent Number: 6,025,197
[45] Date of Patent: Feb. 15, 2000

[54] SECRETED SALIVARY ZSIG32 POLYPEPTIDES

[75] Inventor: Paul O. Sheppard, Redmond, Wash.

[73] Assignee: ZymoGenetics, Inc., Seattle, Wash.

[21] Appl. No.: 09/040,786

[22] Filed: Mar. 18, 1998

Related U.S. Application Data

[60] Provisional application No. 60/041,263, Mar. 19, 1997.

[51] Int. Cl.[7] .............................. C12N 5/10; C12N 15/63; C12N 15/12; C07K 14/435
[52] U.S. Cl. ...................... 435/325; 435/320.1; 530/350; 530/387.1; 536/23.4; 536/23.5; 536/24.1
[58] Field of Search ................................. 435/320.1, 325; 530/350, 387.1; 536/23.4, 23.5, 24.1

[56] References Cited

FOREIGN PATENT DOCUMENTS

96/23080  8/1996  WIPO .

OTHER PUBLICATIONS

Mills et al., *Nucl. Acids Res.* 15: 7709–7723, 1987.

Anderegg et al., *Biochemistry* 27: 4214–4221, 1988.

Girard et al., *J. Biol. Chem.* 268: 26592–26601, 1993.

*Primary Examiner*—John S. Brusca
*Attorney, Agent, or Firm*—Susan E. Lingenfelter

[57] ABSTRACT

The present invention relates to polynucleotide and polypeptide molecules for secreted salivary zsig32 polypeptides. The polypeptides, and polynucleotides encoding them modulate adhesion or modulate or indicate salivary gland function. The present invention also includes antibodies and binding proteins for the zsig32 polypeptides.

20 Claims, 1 Drawing Sheet

```
                        10        20        30        40        50
U00964_1        MFQLEAMLPLLILAFLGTPAVLTQSRYHGSETGKHFCIVAPEGEPVTGIW  44
S76879_1        MFQLEAMLPLLILAFLGTPTVLTQD-YHGPEVGKHSCTSAPEGKNITSIR  49
zsig32-bestorf  MHRPEAMLLLLTLALLGGPT--WAGKMYGPGGGKYFSTTEDYDHEITGLR  48
SPBP_MOUSE      ------MLLLLTLAFLASPTCRAQNVL-GNAAGKYFYVQGEDQGQLKGMR  43

60        70        80        90       100
U00964_1        ASLKN-NILSSIRLKFGNNWSQEYGSSGRAEIEVKLNPDETVLGFSGSFY  93
S76879_1        VFLQG-RSIVGIQFNYNNEDGQVYGSTAGKVMVARLNNEESIIAAEGTYS  98
zsig32-bestorf  VSVGL-LLVKSVQVKLGDSWDVKLGALGGNTQEVTLQPGEYITKVFVAFQ  97
SPBP_MOUSE      IFLSVFKFIKGFQLQFGSNWTDVYGTRSDNFIDFLLEDGEHVIKVEGS-A  92

110       120       130       140       150
U00964_1        IF-MHQIIITTSQPRELIIGPLTGRYVYTSYPENPNHVFRGICGYYVTGG 142
S76879_1        PSALTQIIFTTNQPRQLMVGYYVGSSEYSSFPDDPSHVLKGACVSWRAGG 148
zsig32-bestorf  AF-LRGMVMYTSKDRYFYFGKLDGQ-ISSAYPSQEGQVLVGIYGQYQLLG 145
SPBP_MOUSE      VICLTSLTFTTNKGRVATFGVRRGRY-FSDTGGSDKHLVTVNGMHAPGLC 141

160       170       180       190       200
U00964_1        LKGMRYLWGNVNGTCTE--------------------------------- 159
S76879_1        IKSILFLWGTENSSCVKYGHSG---------------------------- 170
zsig32-bestorf  IKSIGFEWNYPLEEPTTEPPVNLTYSANSPVGR----------------- 178
SPBP_MOUSE      VRGIGFKWGNINANGNDHYNNKEDKADNKDADNKDADNKDDGDEDDDGND 191

210
U00964_1        -------- 159
S76879_1        -------- 170
zsig32-bestorf  -------- 178
SPBP_MOUSE      DDDQKDES 199
```

Figure

SECRETED SALIVARY ZSIG32 POLYPEPTIDES

CROSS REFERENCE TO RELATED APPLICATIONS

This application claims the benefit of U.S. Provisional Application Ser. No. 60/041,263, filed Mar. 19, 1997.

BACKGROUND OF THE INVENTION

The salivary glands synthesize and secrete a number of proteins having diverse biological functions. Such proteins facilitate lubrication of the oral cavity (e.g., mucins and proline-rich proteins), remineralization (e.g., statherin and ionic proline-rich proteins) and digestion (e.g., amylase, lipase and proteases) and provide anti-microbial (e.g., proline-rich proteins, lysozyme, histatins and lactoperoxidase) and mucosal integrity maintenance (e.g., mucins) capabilities. In addition, saliva is a rich source of growth factors synthesized by the salivary glands. For example, saliva is known to contain epidermal growth factor (EGF), nerve growth factor (NGF), transforming growth factor-alpha (TGF-α), transforming growth factor-beta (TGF-β), insulin, insulin-like growth factors I and II (IGF-I and IGF-II) and fibroblast growth factor (FGF). See, for example, Zelles et al., *J. Dental. Res.* 74(12): 1826–32, 1995. Synthesis of growth factors by the salivary gland is believed to be androgen-dependent and to be necessary for the health of the oral cavity and gastrointestinal tract.

Some salivary gland-produced proteins, such as EGF, are believed to have systemic wound healing effects. Effective wound healing appears to require extended exposure of afflicted tissue to growth factors, which may be facilitated in the oral cavity and gastrointestinal tract by mucin at the epithelial/environmental interface acting to capture saliva growth factors. Also, combinations of growth factors, such as those found in saliva, may be necessary for optimal wound healing. Moreover, protease inhibitors, which are also produced by the salivary glands, appear to facilitate growth factor activity.

In addition, saliva contains adhesive proteins having protective properties with regard to infection by exogenous microorganisms. Such adhesive proteins bind exogenous microorganisms and facilitate the degradation or expulsion thereof. From this rich source of biologically relevant proteins, new secreted proteins are sought. Also, given the importance and variety of saliva proteins, conditions involving inadequate saliva production or secretion have inspired investigative effort.

*Rattus norvegicus* common salivary protein 1 (U00964_1) and a murine homolog of common salivary protein 1 (S76879_1) have been discovered and characterized. See, for example, Girard et al., *J. Biol. Chem.* 268(35): 26592–601, 1993. Common salivary protein 1 is so designated as a result of the expression thereof in cells of all major salivary glands. Evidence exists that such expression is androgen-regulated in the rat submandibular gland. Common salivary protein 1 does not include structural features associated with many other salivary proteins, including tandemly repeated sequences, a high density of charged residues and/or an unusually large proportion of a few amino acids. Common salivary protein 1 is somewhat homologous to spermine binding proteins discussed below, but lacks the highly acidic carboxy terminal domain thereof. Thus, the proteins may be evolutionarily related without being functionally related.

Salivary glands share significant features with other glands, such as the prostate gland. For example, the salivary glands and prostate gland are classified as slow replicators with respect to their proliferative capacity. See, for example, Zajicek, *Med. Hypotheses* 7(10): 1241–51, 1981. Such slow replicators exhibit similar onotgenies and proceed during regeneration and neoplasia through similar stages. The prostate gland also appears to produce growth factors, such as EGF and NGF, and other biologically important proteins, such as kallikreins. See, for example, Hiramatsu et al., *Biochem. Int.* 17 (2): 311–7, 1988, Harper et al., *J. Biol. Chem.* 257(14): 8541–8, 1982 and Brady et al., *Biochemistry* 28(12): 5203–10, 1988. Prostate gland function also appears to be androgen-dependent. Consequently, proteins associated with the prostate gland are also sought.

Glandular function is believed to be androgen-dependent. Expression of secreted glycoproteins, having spermine-binding activity, by mouse and rat prostate has also been postulated to be androgen-dependent. See, for example, Mills et al., *Nucleic Acids Res.* 15: 7709–24, 1987. Spermine-binding protein mRNA expression appears to be induced by exposure to androgens, with an increase therein by 2–3 fold being observed within 16 hours and continuing for several days. Thus, intracellular levels of specific hormone-dependent mRNA, such as spermine binding protein mRNA, are useful markers of hormone action. See, Labrie et al., *Endocrinology* 124(6): 2745–54, 1989. Spermine-binding protein is also useful for studying cAMP-independent protein kinases, because the protein is under androgenic control through the action of such kinases. See, for example, Goueli et al., *Biochem. J.* (*England*) 230(2): 293–302, 1985.

Spermine-binding proteins bind to polyamines, such as spermine. Prostatic fluid, for example, is rich in polyamines, and spermine-binding proteins have therefore been postulated to serve as carriers of such polyamines in the seminal fluid. Spermine-binding proteins may also be useful to disrupt spermine-mediated pig lens soluble protein aggregation to form cataracts. See, for example, Maekawa, *Mie. Med. J.* 39(2): 221–8, 1989. In addition, spermine binds to and is believed to modulate the activity of the N-methyl-D-aspartate (NMDA) receptor, a ligand-gated ion channel (Bergeron et al., *J. Med. Chem.* 38: 425–8, 1995). Also, spermine is believed to effect vascular smooth muscle cell contractility via inhibition of myosin phosphatase (Sward et al., *Am. J. Physiology* 269(3 pt. 1): C563–71, 1995). Thus, homologs of spermine-binding proteins are sought.

The present invention provides such polypeptides for these and other uses that should be apparent to those skilled in the art from the teachings herein.

SUMMARY OF THE INVENTION

Within one aspect the invention provides an isolated polypeptide comprising a sequence of amino acid residues that is at least 80% identical in amino acid sequence to residues 23–178 of SEQ ID NO:2. Within one embodiment the polypeptide is at least 90% identical in amino acid sequence to residues 23–178 of SEQ ID NO:2. Within another embodiment the polypeptide comprises residues 27–178 of SEQ ID NO:2. Within yet another embodiment the polypeptide comprises residues 7–178 of SEQ ID NO:2. Within still another embodiment the polypeptide comprises residues 1–178 of SEQ ID NO:2. Within another embodiment the polypeptide is at least 1 kb in length. Within yet another embodiment the polypeptide is covalently linked to a moiety selected from the group consisting of affinity tags, toxins, radionucleotides, enzymes and fluorophores. Within a related embodiment the moiety is an affinity tag selected from the group consisting of polyhistidine, FLAG, Glu—Glu, glutathione S transferase and an immunoglobulin heavy chain constant region. Within another related embodiment the polypeptide further comprises a proteolytic cleavage site between the sequence of amino acid residues and the affinity tag.

Within another aspect is provided an expression vector comprising the following operably linked elements: a transcription promoter; a DNA segment encoding a polypeptide as described above; and a transcriptional terminator. Within a related embodiment the DNA segment encodes a polypeptide covalently linked to an affinity tag selected from the group consisting of polyhistidine, FLAG, Glu—Glu, glutathione S transferase and an immunoglobulin heavy chain constant region. Within a related embodiment the DNA further encodes a secretory signal sequence operably linked to said polypeptide. Within another embodiment the secretory signal sequence encodes residues 7–22 of SEQ ID NO:2. Within a related embodiment the secretory signal sequence encodes residues 1–22 of SEQ ID NO:2. Within another related embodiment is provided a cultured cell into which has been introduced an expression vector as described above, wherein the cell expresses the polypeptide encoded by the DNA segment.

Within another aspect is provided a method of producing a protein comprising: culturing a cell into which has been introduced an expression vector as described above, whereby the cell expresses the protein encoded by the DNA segment; and recovering the expressed protein.

Within another aspect is provided a pharmaceutical composition comprising a polypeptide as described above in combination with a pharmaceutically acceptable vehicle.

Within other aspects are provided an antibody that specifically binds to an epitope of a polypeptide as described above and a binding protein that specifically binds to an epitope of a polypeptide as described above.

Within a further aspect is provided an isolated polynucleotide encoding a polypeptide as described above. Within one embodiment is provided an isolated polynucleotide as described above wherein the polynucleotide is selected from the group consisting of, a) a sequence of nucleotides from nucleotide 168 to nucleotide 704 of SEQ ID NO:1; b) a sequence of nucleotides from nucleotide 186 to nucleotide 704 of SEQ ID NO:2; c) a sequence of nucleotides from nucleotide 234 to nucleotide 704 of SEQ ID NO:2; d) a sequence of nucleotides from nucleotide 246 to nucleotide 704 of SEQ ID NO:2; e) allelic variants of a), b), c) or d); and f) nucleotide sequences complementary to a), b), c), d) or e). Within another embodiment the polynucleotide is from 471 to 853 nucleotides in length. Within another embodiment the polynucleotide comprises nucleotide 1 to nucleotide 534 of SEQ ID NO:20. Within another embodiment the polynucleotide is DNA.

Within another aspect of the invention is provided an oligonucleotide probe or primer comprising 14 contiguous nucleotides of a polynucleotide of SEQ ID NO:20 or a sequence complementary to SEQ ID NO:20.

Within yet another aspect is provided a method for detecting a genetic abnormality in a patient, comprising: obtaining a genetic sample from a patient; incubating the genetic sample with a polynucleotide comprising at least 14 contiguous nucleotides of SEQ ID NO:1 or the complement of SEQ ID NO:1, under conditions wherein said polynucleotide will hybridize to complementary polynucleotide sequence, to produce a first reaction product; comparing said first reaction product to a control reaction product, wherein a difference between said first reaction product and said control reaction product is indicative of a genetic abnormality in the patient.

Within a further aspect is provided a DNA construct encoding a polypeptide fusion, said fusion comprising a secretory signal sequence selected from the group consisting of: (a) amino acid residues 1–22 of SEQ ID NO:2; and (b) amino acid residues 7–22 of SEQ ID NO:2; wherein the secretory signal sequence is operably linked to an additional polypeptide.

Within another aspect is provided a method for detecting zsig32 polypeptides comprising: exposing a polypeptide containing sample to an antibody attached to a solid support, wherein said antibody binds to an epitope of a zsig32 polypeptide; washing said immobilized antibody-polypeptide to remove unbound contaminants; exposing the immobilized antibody-polypeptide to a second antibody directed to a second epitope of a zsig32 polypeptide, wherein the second antibody is associated with a detectable label; and detecting the detectable label.

These and other aspects of the invention will become evident upon reference to the following detailed description of the invention and the attached drawing.

BRIEF DESCRIPTION OF THE DRAWING

The FIGURE illustrates an alignment of mouse ventral prostate spermine-binding protein (SPBP_MOUSE), *Rattus norvegicus* common salivary protein 1 (U00964_1), a murine common salivary protein 1 (S76879_1) and a zsig32 polypeptide of the present invention (SEQ ID Nos. 2–5).

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" denotes any of two or more alternative -orms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of <$10^9$ $M^{-1}$.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, Nature 316:774–78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., greater than 95% pure, more preferably greater than 99% pure.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" denotes a portion of a gene containing DNA sequences that provide for the binding of RNA polymerase and initiation of transcription. Promoter sequences are commonly, but not always, found in the 5' non-coding regions of genes.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, QM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a polypeptide characterized by homology to mouse ventral prostate spermine-binding protein (SEQ ID NO: 3). See, for example, Mills et al., *Nucleic Acids Res.* 15: 7709–24, 1987. Possibly more significant is the homology of zsig32 polypeptide to *Rattus norvegicus* common salivary protein (U00964_1; SEQ ID NO: 4), as discussed in Girard et al.,*J. Biol. Chem.*, 268(35): 26592–601, 1993, and murine common salivary protein 1 (S76879_1; SEQ ID NO: 5).

In addition, the zsig32 polypeptides of the present invention preferably incorporate one potential N-glycosylation site at amino acid 167 (Asn) of SEQ ID NO: 2. Zsig32 polypeptides of the present invention also preferably incorporate two potential tyrosine sulfatation sites at amino acids 40 and 155 of SEQ ID NO: 2. Preferably, one potential protein kinase C phosphorylation site is located at amino acid 107 (Tyr) of SEQ ID NO: 2. Such putative sites of phosphorylation may indicate that zsig32, like spermine-binding protein, is regulated by cAMP-independent protein kinases. See, for example, Goueli et al., *Biochem. J. (England)* 230(2): 293–302, 1985. In addition, the zsig32 polypeptides of the present invention preferably incorporate three potential casein kinase II phosphorylation sites at amino acids 35 (Ser), 36 (Tyr) and 107 (Tyr) of SEQ ID NO: 2 Such sites may indicate that zsig32 may be regulated by casein kinase II. Preferably, three potential N-myristoylation sites are located at amino acids 46, 72 and 120 of SEQ ID NO: 2). These sites are not 100% conserved in the aligned common salivary proteins.

Zsig32 polypeptides also preferably incorporate an adhesion motif (amino acid residues 63–65 of SEQ ID NO: 2). According to three-dimensional analysis of polypeptide structure, the adhesion motif appears to be exposed. Thus, zsig32 polypeptides and fragments thereof, incorporating such an adhesion motif, appear to be useful in the study of adhesion, as is more fully described herein. Also useful in this regard are fusion proteins containing zsig32 polypeptide or an exposed adhesion motif-containing fragment thereof.

The novel polypeptides of the present invention, designated zsig32 polypeptides, were initially identified by querying an EST database for secretory signal sequences characterized by an upstream methionine start site, a hydrophobic region of approximately 13 amino acids and a cleavage site (SEQ ID NO: 6, wherein cleavage occurs between the alanine and glycine amino acid residues) in an effort to select for secreted proteins. Polypeptides corresponding to ESTs meeting those search criteria were compared to known sequences to identify secreted proteins having homology to known ligands. A single EST sequence was discovered and predicted to be related to a secreted spermine-binding protein found in rat ventral prostate (SPBP). See, for example, Mills et al., *Nucleic Acids Res.* 15: 7709–24, 1987. Homology was also discovered between zsig32 polypeptide and *Rattus norvegicus* common salivary protein 1 (U00964_1), as discussed in Girard et al., *J. Biol. Chem.*, 268(35): 26592–601, 1993, and a murine common salivary protein 1 (S76879_1).

The full sequence of the zsig32 polypeptide was obtained from a single clone believed to contain it, wherein the clone was obtained from a parotid gland tissue library. Other libraries that might also be searched for such clones include submandibular gland, salivary gland, prostate, trachea, colon, stomach, prostate tumor, lung, thyroid, tongue tumor and the like.

Analysis of the tissue distribution of the mRNA corresponding to this novel DNA by Northern blot analysis using a synthetic probe (SEQ ID NO: 7) showed that expression was highest in trachea, lower in prostate, and apparent but further decreased in colon and stomach. A tissue distribution analysis by Dot blot showed extremely high expression in salivary gland, with significantly less expression in trachea and apparent but further decreased expression in prostate. In evaluating these results it is important to note that the Northern blot analysis did not include the salivary gland. A single transcript size of approximately 1 kb was observed.

The nucleotide sequence of the N-terminal EST is described in SEQ ID NO: 1, and its deduced amino acid sequence is described in SEQ ID NO: 2. Analysis of the DNA encoding a zsig32 polypeptide (SEQ ID NO: 1) revealed an open reading frame encoding either 178 (Met at amino acid number 1 of SEQ ID NO: 2 is the start site) or 172 amino acids (Met at amino acid number 7 of SEQ ID NO: 2 is the start site). The open reading frame comprises a signal peptide of either 22 amino acid residues (residue 1 to residue 22 of SEQ ID NO: 2; Met at position 1 is the start site) or 16 amino acid residues (residue 7 to residue 22 of SEQ ID NO: 2; Met at position 7 is the start site) and a mature polypeptide of 156 amino acids (residue 23 to residue 178 of SEQ ID NO: 2). Those skilled in the art will recognize that predicted secretory signal sequence domain boundaries are approximations based on primary sequence content, and may vary slightly; however, such estimates are generally accurate to within ±4 amino acid residues. Therefore the present invention also includes the polypeptides having amino acid sequences comprising amino acid residues 20–178 of SEQ ID NO:2, residues 21–178 of SEQ ID NO:2, residues 22–178 of SEQ ID NO:2, residues 23–178 of SEQ ID NO:2, residues 24–178 of SEQ ID NO:2, residues 25–178, residues 26–178 of SEQ ID NO:2 and residues 27–178 of SEQ ID NO:2 as well as the polynucleotides encoding them.

An alignment was prepared including zsig32 polypeptide, mouse ventral prostate spermine-binding protein SPBP_MOUSE (SEQ ID NO: 3; Met at position 7) rat common salivary protein 1 (U00964_1; SEQ ID NO: 4; Met at positions 1 and 7), and murine common salivary protein 1 (S76879_1; SEQ ID NO: 5; Met at positions 1 and 7). That alignment, as shown in the Figure, revealed a block of high percent identity in the signal sequence and a block of significant percent identity in the mature protein corresponding to the region of SEQ ID NO: 2 from amino acid residue 7 (Met), corresponding to aligned residue 7, to amino acid residue 217 (Glu), corresponding to aligned residue 167. When compared, the most conserved sequences are in the signal sequence. Also, the two common salivary proteins and zsig32 share a six amino acid presequence (residues 1–6 of SEQ ID NOS. 4, 5 and 6). In addition, the C-terminal tail of SPBP_MOUSE appears to be longer than that of zsig32 and to be characterized by high asparagine/aspartic acid concentration. The C-terminal tail of SPBP_MOUSE is believed to participate in spermine binding. In contrast, the C-terminal tails of the salivary proteins are shorter than that of zsig32. Neither zsig32 nor the salivary proteins incorporate a region of high asparagine/aspartic acid concentration, potentially indicating alternative regulation or specificity.

Within the region of significant identity in the mature polypeptides, the following percent identity figures are observed for the deduced amino acid sequence of zsig32 polypeptide (SEQ ID NO: 2), SPBP_MOUSE (SEQ ID NO: 3), rat common salivary protein 1, U00964_1 (SEQ ID NO: 4), and murine common salivary protein 1, S76879_1 (SEQ ID NO: 5).

|  | Zsig32 | U00964_1 | S76879_1 | SPBP_MOUSE |
| --- | --- | --- | --- | --- |
| Zsig32 | 100 | 31 | 29 | 29 |
| U00964_1 | 31 | 100 | 44 | 29 |
| S76879_1 | 29 | 44 | 100 | 28 |
| SPBP_MOUSE | 29 | 29 | 28 | 100 |

Highly conserved amino acids can be used as a tool to identify zsig32 polypeptides or other proteins characterized by salivary gland function indication or modulation, spermine or polyamine binding capability, cAMP-independent protein kinase- or androgen-regulation susceptibility or the like. For instance, reverse transcription-polymerase chain reaction (RT-PCR) can be used to amplify sequences encoding a conserved motif from RNA obtained from a variety of tissue sources. In particular, the following primers are useful for this purpose.

1) Amino acids 14–19 of SEQ ID NO: 2 (corresponding to nucleotides 40–57 of SEQ ID NO: 1, nucleotides 40–57 of SEQ ID NO:20 and their complements);
2) Amino acids 31–36 of SEQ ID NO: 2 (corresponding to nucleotides 91–108 of SEQ ID NO: 1, nucleotides 97–108 of SEQ ID NO:20 and their complements);
3) Amino acids 154–159 of SEQ ID NO: 2 (corresponding to nucleotides 460–477 of SEQ ID NO: 1, nucleotides 460–477 of SEQ ID NO:20 and their complements); and
4) Amino acids 109–114 of SEQ ID NO: 2 (corresponding to nucleotides 325–342 of SEQ ID NO: 1, nucleotides 325–342 of SEQ ID NO:20, and their complements).

The activity of polypeptides identified by such probes or of polypeptides encoded by polynucleotides identified by such probes can be determined by methods that are known in the art as generally described herein.

Oligonucleotide probes based on the polynucleotide sequence of SEQ ID NO:1 can be used to localize the zsig32 gene to a particular chromosome. Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, MD http://www.ncbi.nlm. nih.gov), and can be searched with a gene sequence of interest for the mapping data contained within these short genomic landmark STS sequences.

The results of chromosome mapping experiments, as more fully described in Example 3 hereof, showed that the zsig32 gene maps 7.47 cR from the top of the human chromosome 16 linkage group on the WICGR radiation hybrid map. Relative to the centromere, its nearest proximal marker was WI-7742 and its nearest distal maker was WI-3061. The use of surrounding markers positioned the zsig32 gene in the 16p13.3 region on the integrated LDB chromosome 16 map.

The present invention also provides polynucleotide molecules, including DNA and RNA molecules, that encode the zsig32 polypeptides disclosed herein. Those skilled in the art will readily recognize that, in view of the degeneracy of the genetic code, considerable sequence variation is possible among these polynucleotide molecules. SEQ ID NO:20 is a degenerate DNA sequence that encompasses all DNAs that encode the zsig32 polypeptide of SEQ ID NO:2. Those skilled in the art will recognize that the degenerate sequence of SEQ ID NO:20 also provides all RNA sequences encoding SEQ ID NO:2 by substituting U for T.

Thus, zsig32 polypeptide-encoding polynucleotides comprising nucleotide 61 to nucleotide 534 of SEQ ID NO:20, nucleotide 22 to nucleotide 534 of SEQ ID NO:20 and nucleotide 1 to nucleotide 534 of SEQ ID NO:20 and their RNA equivalents are contemplated by the present invention. Table 1 sets forth the one-letter codes used within SEQ ID NO:20 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:20, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine.

Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:20 serves as a template for optimizing express-on of polynucleotides in various cell types and species commonly used in the art and disclosed herein. Sequences containing preferential codons can be tested and optimized for expression in various species, and tested for functionality as disclosed herein.

Based upon homology to spermine binding protein, zsig32 polypeptides may be used in the study of cAMP-independent protein kinases or androgens. Androgens mediate cAMP-independent protein kinase levels, which in turn mediate phospnorylation of zsig32 polypeptides. In an embodiment of the present invention, immobilized zsig32 polypeptides are incubated with $\gamma$-$^{32}$P-ATP and a cAMP-independent protein kinase, and incorporation of $^{32}$P into zsig32 polypeptides is monitored by known techniques. Alternatively, cells that express or are engineered to express zsig32 polypeptides and that endogenously express one or more cAMP-independent protein kinase are incubated with androgens and $\gamma$-$^{32}$P-ATP. The cells are then lysed and incorporation of $^{32}$P into zsig32 polypeptides is monitored by known techniques. In addition, spermine binding protein mRNA has been suggested as a marker for specific androgen activity, as described in Labrie et al., *Endocrinology* 124(6): 2745–54, 1989. Zsig32 polypeptide mRNA may also be useful for that purpose.

As shown in the Figure and described herein, zsig32 polypeptides also exhibit homology to common salivary protein 1 isolated from rat and mouse. Moreover, zsig32 polypeptides are characterized by a limited tissue distribution. While the Northern blot and Dot blot analyses are not in complete agreement, a high level of expression of zsig32 polypeptide was observed in the salivary gland. Consequently, another aspect of the present invention involves the detection of zsig32 polypeptides in the serum or tissue biopsy of a patient undergoing evaluation for salivary gland function or dysfunction. Such zsig32 polypeptides can be detected using immunoassay techniques and antibodies capable of recognizing zsig32 polypeptide epitopes.

More specifically, the present invention contemplates methods for detecting zsig32 polypeptide comprising:

exposing a solution possibly containing zsig32 polypeptide to an antibody attached to a solid support, wherein said antibody binds to a first epitope of a zsig32 polypeptide;

washing said immobilized antibody-polypeptide to remove unbound contaminants;

exposing the immobilized antibody-polypeptide to a second antibody directed to a second epitope of a zsig32 polypeptide, wherein the second antibody is associated with a detectable label; and detecting the detectable label. Serum or biopsy zsig32 polypeptide concentration (relative to normal serum or tissue concentration) may be indicative of dysfunction of the salivary gland. Salivary gland dysfunctions include digestive dysfunction, wound healing dysfunction, inadequate saliva production or composition, mucosal integrity breakdown, failure or diminished anti-microbial function. Detection of zsig32 polypeptide at relatively high levels in the trachea may indicate that such polypeptides may serve as a marker of lung dysfunction. Examples of conditions associated with salivary gland or lung dysfunction include salivary gland carcinoma, sarcoidosis, pneumocystic carinii (particularly as associated with AIDS patients), emphysema, chronic bronchitis, cystic fibrosis, ARDS, SIDS or the like. In addition, zsig32 polypeptides are expressed in the prostate, albeit at a lower level than in the salivary gland and trachea. The prostate gland is androgen regulated and shares other properties with salivary glands. Consequently, dysfunction thereof, such as prostate adenocarcinoma or the like, may also be detected using zsig32 polypeptides.

Also, the salivary glands synthesize and secrete a number of proteins having diverse biological functions. Such proteins facilitate lubrication of the oral cavity (e.g., mucins and proline-rich proteins), remineralization (e.g., statherin and ionic proline-rich proteins), digestion (e.g., amylase, lipase and proteases), provide anti-microbial (e.g., proline-rich proteins, lysozyme, histatins and lactoperoxidase) and mucosal integrity maintenance (e.g., mucins) capabilities. In addition, saliva is a rich source of growth factors synthesized by the salivary glands. For example, saliva is known to contain epidermal growth factor (EGF), nerve growth factor (NGF), transforming growth factor-alpha (TGF-α), transforming growth factor-beta (TGF-β), insulin, insulin-like growth factors I and II (IGF-I and IGF-II) and fibroblast growth factor (FGF). See, for example, Zelles et al., *J. Dental. Res.* 74: 1826–32, 1995. Synthesis of growth factors by the salivary gland is believed to be androgen-dependent and to be necessary for the health of the oral cavity and gastrointestinal tract.

Thus, zsig32 polypeptides, agonists or antagonists thereof may be therapeutically useful for aiding digestion. To verify the presence of this capability in zsig32 polypeptides, agonists or antagonists of the present invention, such zsig32 polypeptides, agonists or antagonists are evaluated with respect to their ability to break down starch according to procedures known in the art. If desired, zsig32 polypeptide performance in this regard can be compared to digestive enzymes, such as amylase, lipase, proteases and the like. In addition, zsig32 polypeptides or agonists or antagonists thereof may be evaluated in combination with one or more digestive enzymes to identify synergistic effects.

Also, zsig32 polypeptides, agonists or antagonists thereof may be therapeutically useful for promoting wound healing. To verify the presence of this capability in zsig32 polypeptides, agonists or antagonists of the present invention, such zsig32 polypeptides, agonists or antagonists are evaluated with respect to their ability to facilitate wound healing according to procedures known in the art. If desired, zsig32 polypeptide performance in this regard can be compared to growth factors, such as EGF, NGF, TGF-α, TGF-β, insulin, IGF-I, IGF-II, fibroblast growth factor (FGF) and the like. In addition, zsig32 polypeptides or agonists or antagonists thereof may be evaluated in combination with one or more growth factors to identify synergistic effects.

In addition, zsig32 polypeptides, agonists or antagonists thereof may be therapeutically useful for anti-microbial applications. To verify the presence of this capability in zsig32 polypeptides, agonists or antagonists of the present invention, such zsig32 polypeptides, agonists or antagonists are evaluated with respect to their anti-microbial properties according to procedures known in the art. See, for example, Barsum et al., *Eur. Respir. J.* 8: 709–14, 1995; Sandovsky-Losica et al., *J. Med. Vet. Mycol.* (*England*) 28: 279–87, 1990; Mehentee et al., *J. Gen. Microbiol* (*England*) 135 (Pt. 8): 2181–8, 1989; Segal and Savage, *J. Med. Vet. Mycol.* 24: 477–9, 1986 and the like. If desired, zsig32 polypeptide performance in this regard can be compared to proteins known to be functional in this regard, such as proline-rich proteins, lysozyme, histatins, lactoperoxidase or the like. In addition, zsig32 polypeptides or agonists or antagonists thereof may be evaluated in combination with one or more anti-microbial agents to identify synergistic effects.

Anti-microbial protective agents may be directly acting or indirectly acting. Such agents operating via membrane association or pore forming mechanisms of action directly attach to the offending microbe. Anti-microbial agents can also act via an enzymatic mechanism, breaking down microbial Protective substances or the cell wall/membrane thereof. Anti-microbial agents, capable of inhibiting microorganism proliferation or action or of disrupting microorganism integrity by either mechanism set forth herein, are useful in methods for preventing contamination in cell culture by microbes susceptible to that anti-microbial activity. Such techniques involve culturing cells in the presence of an effective amount of said zsig32 polypeptide or an agonist or antagonist thereof.

Also, zsig32 polypeptides or agonists thereof may be used as cell culture reagents in in vitro studies of exogenous microorganism infection, such as bacterial, viral or fungal infection. Such moieties may also be used in in vivo animal models of infection. Also, the microorganism-adherence properties of zsig32 polypeptides or agonists thereof can be studied under a variety of conditions in binding assays and the like.

Moreover, zsig32 polypeptides, agonists or antagonists thereof may be therapeutically useful for mucosal integrity maintenance. To verify the presence of this capability in zsig32 polypeptides, agonists or antagonists of the present invention, such zsig32 polypeptides, agonists or antagonists are evaluated with respect to their mucosal integrity maintenance according to procedures known in the art. See, for example, Zahm et al., *Eur. Respir. J.* 8: 381–6, 1995, which describes methods for measuring viscoelastic properties and surface properties of mucous as well as for evaluating mucous transport by cough and by ciliary activity. If desired, zsig32 polypeptide performance in this regard can be compared to mucins or the like. In addition, zsig32 polypeptides or agonists or antagonists thereof may be evaluated in combination with mucins to identify synergistic effects.

In addition, a 37 amino acid peptide has been discovered which is secreted in saliva and believed to cause vasodilation of cranial blood vessels. Such vasodilation leads to migrane attacks. This peptide is believed to be secreted in response to clenching of the teeth, which is also often associated with migrane attacks. Thus, a further aspect of the present invention involves the determination of the vasodilatory effects of zsig32 polypeptides and agonists and antagonists thereof. Such determination may be made using known assay techniques. Compounds capable of down-modulating vasodilation of blood vessels may be useful in the prevention or treatment of migrane attacks.

Polynucleotides encoding zsig32 polypeptides are useful within gene therapy applications where it is desired to increase or inhibit zsig32 activity. If a mammal has a mutated or absent zsig32 gene, the zsig32 gene can be introduced into the cells of the mammal. In one embodiment, a gene encoding a zsig32 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:526–30, 1992; and a defective adeno-associated virus vector (Samulski et al., *J. Virol.* 61:3096–101, 1987; Samulski et al., *J. Virol.* 63:3822–8, 1989).

In another embodiment, a zsig32 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication NO: WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zsig32 gene transcription, such as to inhibit cell proliferation in vivo. Polynucleotides that are complementary to a segment of a zsig32-encoding polynucleotide (e.g., a polynucleotide as set froth in SEQ ID NO:1) are designed to bind to zsig32-encoding mRNA and to inhibit translation of such mRNA. Such antisense polynucleotides are used to inhibit expression of zsig32 polypeptide-encoding genes in cell culture or in a subject.

Transgenic mice, engineered to express the zsig32 gene, and mice that exhibit a complete absence of zsig32 gene function, referred to as "knockout mice" (Snouwaert et al., *Science* 257:1083, 1992), may also be generated (Lowell et al., *Nature* 366:740–42, 1993). These mice may be employed to study the zsig32 gene and the protein encoded thereby in an in vivo system.

The present invention also provides reagents for use in diagnostic applications. For example, the zsig32 gene, a probe comprising zsig32 DNA or RNA, or a subsequence thereof can be used to determine if the zsig32 gene is present on chromosome 16 or if a mutation has occurred. Detectable chromosomal aberrations at the zsig32 gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA—RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

Within another aspect of the present invention there is provided a pharmaceutical composition comprising purified zsig32 polypeptide in combination with a pharmaceutically acceptable vehicle. Such pharmaceutical compositions may be administered to prevent or treat salivary gland dysfunction. Such prevention or treatment may be directed to digestive dysfunction, such as a deficiency in starch breakdown capability or efficiency, wound healing dysfunction, inadequate saliva production or composition or mucosal integrity breakdown. Zsig32 polypeptides may also have an anti-microbial function, most likely stemming from an exposed adhesion motif as discussed herein. Also, expression of zsig32 polypeptide at a relatively high level in trachea may indicate a role for zsig32 polypeptides in prevention or treatment of destructive lung disease. Examples of pathological conditions, characterized by one or more of the aforementioned criteria, include xerostomia, sarcoidosis, dental caries, osteomyelitis, oral candidiasis, buccal mucosa infections, chronic inflammation (Siogren's syndrome), mumps, chronic bronchitis, adult respiratory distress syndrome LARDS), sudden infant death syndrome (SIDS), salivary gland carcinoma, pneumocystic carinii (particularly as associated with AIDS patients), cystic fibrosis, emphysema and the like.

Evaluation of zsig32 polypeptide involvement in such conditions may be conducted using in vivo or in vitro methods that are known to those of ordinary skill in the art. For example, bronchoalveolar lavage may be employed in the assessment of destructive lung diseases, such as pulmonary emphysema, chronic bronchitis, cystic fibrosis, ARDS and the like. See, for example, Luisetti et al., *Respiration* 59(suppl. 1): 24–7, 1992. Salivary gland, lacrimal gland and labial salivary gland biopses may be employed in the evaluation of xerostomia. See, for example, Matsumoto et al., *J. Clin. Invest.* 97(8): 1969–77, 1996. This calcium channel dependent condition has also been evaluated using fura-2 assays of intracellular calcium ion concentration, as described in Seagrave et al., *Archs. Oral Biol.* 41(5): 425–30, 1996. Alymphoplasia (aly) mice are a useful animal model for systemic Sjogren's syndrome, an autoimmune disease characterized by lymphocytic infiltration into the lachrymal and salivary glands, leading to symptomatic dry eyes and mouth. See, for example, Furukawa et al., *Brit. J. Rheum.* 35: 1223–30, 1996.

The present invention provides methods for identifying agonists or antagonists of the zsig32 polypeptides disclosed herein, which agonists or antagonists may have valuable therapeutic properties as discussed further herein. Within one embodiment, there is provided a method of identifying zsig32 polypeptide agonists, comprising providing cells responsive to a zsig32 polypeptide as disclosed herein, culturing the cells in the presence of a test compound and comparing the cellular response with the cell cultured in the presence of the zsig32 polypeptide, and selecting the test compounds for which the cellular response is of the same type. Agonists are therefore useful to mimic or augment the function of zsig32 polypeptides.

Within another embodiment, there is provided a method of identifying antagonists of zsig32 polypeptide, comprising providing cells responsive to a zsig32 polypeptide, culturing a first portion of the cells in the presence of zsig32 polypeptide, culturing a second portion of the cells in the presence of the zsig32 polypeptide and a test compound, and detecting a decrease in a cellular response of the second portion of the cells as compared to the first portion of the cells. Antagonists are therefore useful to inhibit or diminish zsig32 polypeptide function.

Zsig32 polypeptides of the present invention exhibit an adhesion motif at amino acid residues 63–65 of SEQ ID NO: 2. According to three-dimensional analysis of polypeptide structure, the adhesion motif appears to be exposed. Thus, zsig32 polypeptides, fragments thereof incorporating such an adhesion motif or fusion proteins incorporating zsig32 polypeptide or the adhesion motif-containing fragment thereof appear to be useful in the study of adhesion. Such study can be accomplished using a method of modulating adhesion of platelets, for example, in cell culture, comprising incubating platelets in a culture medium comprising a zsig32 polypeptide as disclosed above in an amount sufficient to modulate adhesion. Assays for evaluation of platelet adhesion are known in the art.

Zsig32 polypeptides or antagonists or agonists thereof are expected be useful in circumstances where modulation of adhesion is desired. Such adhesion-modulating function may be used in in vitro experiments designed to study adhesion, such as adhesion of microorganisms to cells, tissue or mucous. Enhancers and inhibitors of adhesion also have potential as therapeutics for conditions requiring such modulation. For example, enhanced tumor cell-tumor cell adhesion in a primary solid tumor does not favor metastasis thereof. Also, diminished tumor cell-endothelial cell adhesion also does not favor metastasis formation at a site distant from the primary tumor. Assays to assess metastatic potential, assessed using adhesion parameters, are known in the art. See, for example, Koenigsmann et al., *Onkologie* 17: 528–37, 1994, Asao et al., *Canc. Letts.* 78: 57–62, 1994 and the like.

A still further aspect of the invention provides useful research reagents and methods for evaluating salivary gland function. Zsig32 polypeptides, agonists or antagonists thereof can be admixed with test saliva or one or more proteins contained in saliva to provide culture conditions under which salivary gland function can be studied. For example, admixture of zsig32 polypeptides, agonists or antagonists thereof can be combined with one or more growth factors to provide a culture medium in which the wound healing properties of saliva can be studied.

Within preferred embodiments of the invention the isolated polynucleotides will hybridize to similar sized regions of SEQ ID NO: 2, SEQ ID NO: 6, SEQ ID NO: 10, or SEQ ID NO: 11, the other specific probes referred to herein, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is less than about 0.02 M at pH 7 and the temperature is at least about 60° C.

As previously noted, the isolated zsig32 polynucleotides of the present invention include DNA and RNA. Methods for isolating DNA and RNA are well known in the art. It is generally preferred to isolate RNA from salivary gland tissues, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–12, 1972). Complementary DNA (cDNA) is prepared from poly$(A)^+$ RNA using known methods. Polynucleotides encoding zsig32 polypeptides are hen identified and isolated by, for example, hybridization or PCR.

The present invention further provides counterpart polypeptides and polynucleotides from other species (orthologs). These species include, but are not limited to mammalian, avian, amphibian, reptile, fish, insect and other vertebrate and invertebrate species. Of particular interest are zsig32 polypeptides from other mammalian species, including murine, rat, porcine, ovine, bovine, canine, feline, equine and other primate proteins. Species homologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a posizive tissue of cell line. A zsig32-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to an epitope of a zsig32 polypeptide. Similar techniques can also be applied to the isolation of genomic clones.

Those skilled in the art will recognize that the sequences disclosed in SEQ ID NO:1 and SEQ ID NO:2 represent a single allele of the human zsig32 gene and polypeptide, and that allelic variation and alternative splicing are expected to occur. Allelic variants can be cloned by probing cDNA or genomic libraries from different individuals according to standard procedures. Allelic variants of the DNA sequence shown in SEQ ID NO: 1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zsig32 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zsig32 polypeptides that are substantially homologous to the polypeptides of SEQ ID NO:2 and their orthologs. The term "substantially homologous" is used herein to denote polypeptides having 50%, preferably 60%, more preferably at least 80%, sequence identity to the sequences shown in SEQ ID NO:2 or the orthologs. Such polypeptides will more preferably be at least 90% identical, and most preferably 95% or more identical to SEQ ID NO:2 or its orthologs. Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| A | 4  |    |    |    |    |    |    |    |    |    |    |    |    |    |    |    |    |    |    |   |
| R | -1 | 5  |    |    |    |    |    |    |    |    |    |    |    |    |    |    |    |    |    |   |
| N | -2 | 0  | 6  |    |    |    |    |    |    |    |    |    |    |    |    |    |    |    |    |   |
| D | -2 | -2 | 1  | 6  |    |    |    |    |    |    |    |    |    |    |    |    |    |    |    |   |
| C | 0  | -3 | -3 | -3 | 9  |    |    |    |    |    |    |    |    |    |    |    |    |    |    |   |
| Q | -1 | 1  | 0  | 0  | -3 | 5  |    |    |    |    |    |    |    |    |    |    |    |    |    |   |
| E | -1 | 0  | 0  | 2  | -4 | 2  | 5  |    |    |    |    |    |    |    |    |    |    |    |    |   |
| G | 0  | -2 | 0  | -1 | -3 | -2 | -2 | 6  |    |    |    |    |    |    |    |    |    |    |    |   |
| H | -2 | 0  | 1  | -1 | -3 | 0  | 0  | -2 | 8  |    |    |    |    |    |    |    |    |    |    |   |
| I | -1 | -3 | -3 | -3 | -1 | -3 | -3 | -4 | -3 | 4  |    |    |    |    |    |    |    |    |    |   |
| L | -1 | -2 | -3 | -4 | -1 | -2 | -3 | -4 | -3 | 2  | 4  |    |    |    |    |    |    |    |    |   |
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or an affinity tag. Polypeptides comprising affinity tags can further comprise a proteolytic cleavage site between the zsig32 polypeptide and the affinity tag. Preferred such sites include thrombin cleavage sites and factor Xa cleavage sites.

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions [and related multimeric proteins comprising one or more polypeptide fusions]. For example, a zsig32 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zsig32 polypeptide fusions can be expressed in genetically engineered cells [to produce a variety of multimeric zsig32 analogs]. Auxiliary domains can be fused to zsig32 polypeptides to target them to specific cells, tissues, or macromolecules. For example, a zsig32 polypeptide or protein could be targeted to a predetermined cell type by fusing a zsig32 polypeptide to a ligand that specifically binds to a receptor on the surface of the target cell. In this way, polypeptides and proteins can be targeted for therapeutic or diagnostic purposes. A zsig32 polypeptide can be fused to two or more moieties, such as an affinity tag for purification and a targeting domain. Polypeptide fusions can also comprise one or more cleavage sites, particularly between domains. See, Tuan et al., *Connect. Tiss. Res.* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured On the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zsig32 amino acid residues.

Essential amino acids in the zsig32 polypeptides of the present invention can be identified according to procedures known in the art, such as site-directed mutagenesis or alanine-scanning mutagenesis (Cunningham and Wells, *Science* 244: 1081–5, 1989). In the latter technique, single alanine mutations are introduced at every residue in the molecule, and the resultant mutant molecules are tested for biological activity (e.g., androgen regulation, anti-microbial activity, adhesion modulation or the like) to identify amino acid residues that are critical to the activity of the molecule. See also, Hilton et al., *J. Biol. Chem.* 271:4699–708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related proteins.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants cf the disclosed zsig32 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., those susceptible to androgen regulation, capable of anti-microbial action or adhesion modulation or the like) can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptides that are substantially homologous to residues 23 (Gly) to 178 (Arg) of SEQ ID NO: 2 or allelic variants thereof and retain the one or more properties of the wild-type protein. Such polypeptides may include additional amino acids, such as affinity tags or the like. Such polypeptides may also include additional polypeptide segments as generally discussed herein.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrock et al., *Molecular Cloning: A Laboratory Manual*, 2nd ed., Cold Spring Harbor Laboratory Press, Cold Spring Harbor, N.Y., 1989, and Ausubel et al. (eds.), *Current Protocols in Molecular Biology*, John Wiley and Sons, Inc., NY, 1987.

In general, a DNA sequence encoding a zsig32 polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig32 polypeptide into the secretory pathway of a host cell, a secretory signal sequence (also known as a leader sequence, prepro sequence or pre sequence) is provided in the expression vector. The secretory signal sequence may be that of the zsig32 polypeptide, or may be derived from another secreted protein (e.g., t-PA) or synthesized de novo. The secretory signal sequence is joined to the zsig32-encoding DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830). Conversely, the signal sequence portion of the zsig32 polypeptide (amino acids 1–22 or 7–22 of SEQ ID NO: 2) may be employed to direct the secretion of an alternative protein by analogous methods.

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), liposome-mediated transfection (Hawley-Nelson et al., *Focus* 15:73, 1993; Ciccarone et al., *Focus* 15:80, 1993), and viral vectors (Miller and Rosman, *BioTechniques* 7:980–90, 1989; Wang and Finer, *Nat. Med.* 2:714–16, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC NO: CRL 1650), COS-7 (ATCC NO: CRL 1651), BHK 570 (ATCC NO: CRL 10314), 293 (ATCC NO: CRL 1573; Graham et al., *J. Gen. Virol.* 36:59–72, 1977) and Chinese hamster ovary (e.g. CHO-KL1; ATCC NO: CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601, 978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including insect cells, plant cells and avian cells. The use of

*Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463. Insect cells can be infected with recombinant baculovirus, commonly derived from *Autographa californica* nuclear polyhedrosis virus (ACNPV). DNA encoding the zsisg32 polypeptide is inserted into the baculoviral genome in place of the ACNPV polyhedrin gene coding sequence by one of two methods. The first is the traditional method of homologous DNA recombination between wild-type AcNPV and a transfer vector containing the zsig32 flanked by ACNPV sequences. Suitable insect cells, e.g. SF9 cells, are infected with wild-type AcNPV and transfected with a transfer vector comprising a zsig32 polynucleotide operably linked to an AcNPV polyhedrin gene promoter, terminator, and flanking sequences. See, King, and Possee, *The Baculovirus Expression System: A Laboratory Guide*, London, Chapman & Hall; O'Reilly et al., *Baculovirus Expression Vectors: A Laboratory Manual*, New York, Oxford University Press., 1994; and, Richardson, Ed., *Baculovirus Expression Protocols. Methods in Molecular Biology*, Totowa, N.J., Humana Press, 1995. Natural recombination within an insect cell will result in a recombinant baculovirus which contains zsig32 driven by the polyhedrin promoter. Recombinant viral stocks are made by methods commonly used in the art.

The second method of making recombinant baculovirus utilizes a transposon-based system described by Luckow (Luckow, et al., *J. Virol.* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zsig32 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zsig32. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins and Possee, *J. Gen. Virol.* 71:971–6, 1990; Bonning et al., *J. Gen. Virol.* 75:1551–6, 1994; and, Chazenbalk and Rapoport, *J. Biol. Chem.* 270:1543–9, 1995. In such transfer vector constructs, a short or long version of the basic protein promoter can be used. Moreover, transfer vectors can be constructed which replace the native zsig32 secretary signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zsig32 secretory signal sequence. In addition, transfer vectors can include an in-frame fusion with DNA encoding an epitope tag at the C- or N-terminus of the expressed zsig32 polypeptide, for example, a Glu—Glu epitope tag (Grussenmeyer et al., ibid.). Using techniques known in the art, a transfer vector containing zsig32 is transformed into *E. coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zsig32 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2–5\times10^5$ cells to a density of $1–2\times10^6$ cells at which time a recombinant viral stock is added at a multiplicity of infection (MOI) of 0.1 to 10, more typically near 3. The recombinant virus-infected cells typically produce the recombinant zsig32 polypeptide at 12–72 hours post-infection and secrete it with varying efficiency into the medium. The culture is usually harvested 48 hours post-infection. Centrifugation is used to separate the cells from the medium (supernatant). The supernatant containing the zsig32 polypeptide is filtered through micropore filters, usually 0.45 $\mu$m pore size. Procedures used are generally described in available laboratory manuals (King and Possee, ibid.; O'Reilly, et al., ibid.; Richardson, ibid.). Subsequent purification of the zsig32 polypeptide from the supernatant can be achieved using methods described herein.

Fungal cells, including yeast cells, and particularly cells of the genus Saccharomyces, can also be used within the present invention, such as for producing zsig32 polypeptide fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasasi et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltose* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribcsyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zsig32 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Expressed recombinant zsig32 polypeptides (or chimeric zsig32 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, Affinity Chromatography: Principles & Methods, Pharmacia LKB Biotechnology, Uppsala, Sweden, 1988.

The polypeptides of the present invention can be isolated by exploitation of their structural properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, Glu—Glu, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zsig32 polypeptides or fragments thereof may also be prepared through chemical synthesis. Zsig32 polypeptides may be monomers or multimers; glycosylated or non-glycosylated; pegylated or non-pegylated; and may or may not include an initial methionine amino acid residue.

A zsig32 polypeptide binding protein can also be used in purification applications. The binding protein is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand (e.g., zsig32 polypeptide) to bind to the receptor/binding protein. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

Zsig32 can be measured in vitro using cultured cells or in vivo by administering molecules of the claimed invention to the appropriate animal model. For instance, zsig32 transfected (or co-transfected) expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5\times10^5$ to about $5\times10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and Douglas and Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will en er the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293S cell production protocol, non-secreted proteins may also be effectively obtained. Zsig32 polypeptides can also be used to prepare antibodies that specifically bind to zsig32 epitopes, peptides or polypeptides. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, hamsters, guinea pigs and rats as well as transgenic animals such as transgenic sheep, cows, goats or pigs. Antibodies may also be expressed in yeast and fungi in modified forms as well as in mammalian and insect cells. The zsig32 polypeptide or a fragment thereof serves as an antigen (immunogen, to inoculate an animal or elicit an immune response. Suitable antigens would include the zsig32 polypeptide encoded by SEQ ID NO:2 from amino acid residue 21–175 of SEQ ID NO:2, or a contiguous 9–175 amino acid residue fragment thereof. The immunogenicity of a zsig32 polypeptide may be increased through the use of an adjuvant, such as alum (aluminum hydroxide) or Freund's complete or incomplete adjuvant. Polypeptides useful for immunization also include fusion polypeptides, such as fusions of zsig2 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hetocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating he entire non-human variable domains (optionally "cloaking" them with a human-like surface by replacement of exposed residues, wherein the result is a "veneered" antibody) in some instances, humanized antibodies may retain non-human residues within the human variable region framework domains to enhance proper binding characteristics. Through humanizing antibodies, biological half-life may be increased, and the potential for adverse immune reactions upon administration to humans is reduced. Human antibodies can also be made in mice having a humanized humoral immune system (Mendez et al., *Nat. Genet.* 14:146–56, 1997).

Alternative techniques for generating or selecting antibodies useful herein include in vitro exposure of lymphocytes to zsig32 protein or peptide, and selection of antibody display libraries, in phage or similar vectors (for instance, through use of immobilized or labeled zsig32 protein or peptide). Mutagenesis methods discussed herein, in particular domain shuffling, can be used to generate and mature antibodies.

The antibodies of the current invention, or fragments thereof, can be used to direct molecules to a specific target. For example, as T-bodies, chimeric receptors combining antibody recognition with T cell effector function, (Eshhar et al., *Springer Semin Immunopathol.* 18:179–209, 1996; Eshhar, *Cancer Immunol. Immunother.* 45:131–6, 1997). Intrabodies, engineered single-chain antibodies expressed inside the cell and having high affinity and specificity for intracellular targets. Such molecules have use in gene therapy and treatment of infectious diseases (Marasco, *Immunotechnology* 1:1–19, 1995; Marasco et al., *Gene Ther.* 4:11–5, 1997; Rondon and Marasco, *Annu. Rev. Microbiol.* 51:257–83, 1997 and Mhashilkar et al.,*J. Virol.* 71:6486–94, 1997). Diabodies, bispecific non-covalent dimers of scFv antibodies useful for immunodiagnosis and therapeutically. In addition they can be constructed in bacteria (Holliger et al., *Proc. Natl. Acad. Sci. USA* 90:6444–48, 1993).

Antibodies herein specifically bind if they bind to a zsig32 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, ibid.).

Genes encoding polypeptides having potential zsig32 polypeptide binding domains, "binding proteins", can be obtained by screening random or directed peptide libraries displayed on phage (phage display) or on bacteria, such as *E. coli*. Nucleotide sequences encoding the polypeptides can be obtained in a number of ways, such as through random mutagenesis and random polynucleotide synthesis. Alternatively, constrained phage display libraries can also be produced. These peptide display libraries can be used to screen for peptides which interact with a known target which can be a protein or polypeptide, such as a ligand or receptor, a biological or synthetic macromolecule, or organic or inorganic substances. Techniques for creating and screening such peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Peptide display libraries can be screened using the zsig32 sequences disclosed herein to identify proteins which bind to zsig32. These "binding proteins" which interact with zsig32 polypeptides can be used essentially like an antibody, for tagging cells; for isolating homolog polypeptides by affinity purification; directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. To increase the half-life of these binding proteins, they can be conjugated. Their biological properties may be modified by dimerizing or multimerizing for use as agonists or antagonists.

A variety of assays known to those skilled in the art can be utilized to detect antibodies and/or binding proteins which specifically bind to zsig32 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zsig32 protein or polypeptide.

Antibodies and binding proteins to zsig32 may be used for tagging cells that express zsig32; for isolating zsig32 by affinity purification; for diagnostic assays for determining circulating levels of zsig32 polypeptides; for detecting or quantitating soluble zsig32 as marker of underlying pathology or disease; in analytical methods employing FACS; for screening expression libraries; for generating anti-idiotypic antibodies; and as neutralizing antibodies or as antagonists to block zsig32 polypeptide adhesion modulating or anti-microbial or like activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zsig32 or fragments thereof may be used in vitro to detect denatured zsig32 or fragments thereof in assays, for example, Western Blots or other assays known in the art.

In another embodiment, polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates. The bioactive polypeptide or antibody conjugates described herein can be delivered intravenously, intraarterially, intraductally with DMSO, intramuscularly, subcutaneously, intraperitoneally, also by transdermal methods, by electro-transfer, orally or via inhalant.

Molecules of the present invention can be used to identify and isolate receptors involved in salivary gland function or saliva composition. For example, proteins and peptides of the present invention can be immobilized on a column and membrane preparations run over the column (*Immobilized Affinity Ligand Techniques*, Hermanson et al., eds., Academic Press, San Diego, Calif., 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zsig32 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLES

Example 1

Extension of EST Sequence

The novel zsig32 polypeptide-encoding polynucleotides of the present invention were initially identified by querying an EST database for secretory signal sequences characterized by an upstream methionine start site, a hydrophobic region of approximately 13 amino acids and a cleavage site (SEQ ID NO: 6, wherein cleavage occurs between the alanine and glycine amino acid residues) in an effort to select for secreted proteins. Polypeptides corresponding to ESTs meeting those search criteria were compared to known sequences to identify secreted proteins having homology to known ligands. A single EST sequence was discovered and predicted to be related to a mouse ventral prostate spermine-binding protein (SPBP) See, for example, Mills et al. cited above. To identify the corresponding cDNA, a clone considered likely to contain the entire coding region was used for sequencing. Using an Invitrogen S.N.A.P.™ Miniprep kit (Invitrogen, Corp., San Diego, Calif.) according to manufacturer's instructions a 5 ml overnight culture in LB+50 μg/ml ampicillin was prepared. The template was sequenced on an ABIPRISM™ model 377 DNA sequencer (Perkin-Elmer Cetus, Norwalk, Conn.) using the ABI PRISM™ Dye Terminator Cycle Sequencing Ready Reaction Kit (Perkin-Elmer Corp.) according to manufacturer's instructions. Oligonucleotides ZC694 (SEQ ID NO: 8), ZC695 (SEQ ID NO:

9) to the T7 and SP6 promoters on the clone-containing vector were used as sequencing primers. Oligonucleotides ZC13183 (SEQ ID NO: 10), ZC13187 (SEQ ID NO: 11) were used t-o complete the sequence from the clone. Sequencing reactions were carried out in a Hybaid Omni-Gene Temperature Cycling System (National Labnet Co., Woodbridge, N.Y.). SEQUENCHER™ 3.0 sequence analysis software (Gene Codes Corporation, Ann Arbor, Mich.) was used for data analysis. The resulting 853 bp sequence is disclosed in SEQ ID NO: 1.

Example 2

Tissue Distribution

Northerns were performed using Human Multiple Tissue Blots from Clontech (Palo Alto, Calif.). A 40 bp DNA probe (ZC12493; SEQ ID NO: 7) to the 5' end of the oligonucleotide sequence of the mature polypeptide shown in SEQ ID NO: 1 was radioactively labeled with $^{32}P$ using T4 polynucleotide kinase and forward reaction buffer (GIBCO BRL, Gaithersburg, Md.) according to the manufacturer's specifications. The probe was purified using a NUCTRAP push column (Stratagene Cloning Systems, La Jolla, Calif.) EXPRESSHYB (Clontech, Palo Alto, Calif.) solution was used for prehybridization and as a hybridizing solution for the Northern blots. Hybridization took place overnight at 42° C., and the blots were then washed in 2× SSC and 0.05% SDS at RT, followed by a wash in 1× SSC and 0.1% SDS at 71° C. One transcript size was observed at approximately 650 bp. Signal intensity was highest for prostate, stomach and trachea, with relatively less intense signals in spleen and colon.

A RNA Master Dot Blot (Clontech) that contained RNAs from various tissues that were normalized to 8 housekeeping genes was also probed with the 40 bp DNA probe (SEQ ID NO: 7). The blot was prehybridized and then hybridized overnight with $10^6$ cpm/ml of the probe at 42° C., according to the manufacturer's specifications. The blot was washed with 2× SSC and 0.05% SDS at RT, followed by a wash in 0.1× SSC and 0.1% SDS at 71° C. After a 48 hour exposure, highest expression was seen in the salivary gland, with much weaker signals in trachea and still weaker signals in prostate. Note that in prostate and trachea, a 2 kb band was also observed.

Example 3

Chromosomal Assignment and Placement of zsig32

Zsig32 was mapped to chromosome 16 using the commercially available GeneBridge 4 Radiation Hybrid Panel (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zsig32 with the GeneBridge 4 RH Panel, 20 µl reactions were set up in a 96-well microtiter plate :Stratagene) and used in a RoboCycler Gradient 96 thermal cycler (Stratagene) Each of the 95 PCR reactions consisted of 2 µl 10× KlenTaq PCR reaction buffer (Clontech), 1.6 µl dNTPs mix (2.5 mM each, PERKIN-ELMER, Foster City, Calif.), 1 µl sense primer, ZC 13,703 (SEQ ID NO:21), 1 µl antisense primer, ZC 13,704 (SEQ ID NO:22), 2 µl RediLoad (Research Genetics, Inc.), 0.4 µl 50× Advantage KlenTaq Polymerase Mix (Clontech Laboratories, Inc.), 25 ng of DNA from an individual hybrid clone or control and ddH$_2$O for a total volume of 20 µl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 60° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed that Zsig32 maps 7.47 cR_3000 from the framework marker WI-7742 on the WICGR chromosome 16 radiation hybrid map. Proximal and distal framework markers were WI-7742 (D16S2960) and WI-3061 (D16S2965), respectively. The use of surrounding markers positions Zsig32 in the 16p13.3 region on the integrated LDB chromosome 16 map (The Genetic Location Database, University of Southhampton, WWW server: http://cedar.genetics.soton.ac.uk/public_html/).

Example 4

Creation of Mammalian Expression Vectors zsig32NF/pZP9, zsig32CF/pZP9 and zsig32/pZP9

Three expression vectors were prepared for the zsig32 polypeptide, zSIG32CF/pZP9 and zSIG32NF/pZP9, wherein the constructs are designed to express a zsig25 polypeptide with a C- or N-terminal FLAG tag (SEQ ID NO: 16) and zSIG32/pZP9 expressing untagged zsig32 polypeptides.

ZSIG32/pZP9

A approximately 800 bp restriction digest fragment of ZSIG-32 DNA was derived from the clone described in Example 1 above. Ten microliters of the clone was digested with 1.5 µl each of the restriction enzymes Eco RI and Not I. The resultant ligation fragment was then run on a 0.8% LMP agarose gel (Seaplaque GTG) with 0.5× TBE buffer. A band of the predicted size was excised and the DNA was purified from the gel with a QIAQUICK® column (Qiagen) according the manufacturer's instructions.

The excised, restriction digested zsig32 DNA was subcloned into plasmid pZP9 which had been cut with Eco RI and Not I. Plasmid CF/pZP9 (deposited at the American Type Culture Collection, 12301 Parklawn Drive, Rockville, Md.) is a mammalian expression vector containing an expression cassette having the mouse metallothionein-1 promoter, multiple restriction sites for insertion of coding sequences, a stop codon and a human growth hormone terminator. The plasmid also has an *E. coli* origin of replication, a mammalian selectable marker expression unit having an SV40 promoter, enhancer and origin of replication, a DHFR gene and the SV40 terminator.

zSIG25CF/pZP9

A 553 bp PCR generated ZSIG-32 DNA fragment was created using ZC13465 (SEQ ID NO:23) and ZC13447 (SEQ ID NO:26) as PCR primers and the template described in Example 1 above. The PCR reaction was incubated at 94° C. for 5 minutes, and then run for 10 cycles of 30 seconds at 94° C. and 2 minutes at 72° C., followed by 15 cycles at 94° C. for 30 seconds and 65° C. for 2 minutes. The resultant PCR product was then run on a 0.9% GTG/TBE agarose gel with 1× TBE buffer. A band of the predicted size was excised and the DNA was purified from the gel with a QIAQUICK® column (Qiagen) according the manufacturer's instructions. The DNA was digested with the restriction enzymes BAM HI (Boehringer Mannheim) and Eco RI (Gibco BRL), followed by phenol/chloroform/isoamyl alcohol extraction and ETOH/glycogen precipitated.

The excised, restriction digested zsig32 DNA was subcloned into plasmid CF/pZP9 which had been cut with Eco RI and Bam HI. The zSIG32/CFpZP9 expression vector uses the native zSIG32 signal peptide, and the FLAG epitope (SEQ ID NO:16) is attached at the C-terminus as a purification aid. Plasmid CF/pZP9 (deposited at the American Type Culture Collection, 12301 Parklawn Drive, Rockville, Md.) is a mammalian expression vector containing an expression cassette having the mouse metallothionein-1 promoter, multiple restriction sites for insertion of coding sequences, a sequence encoding the FLAG tag (SEQ ID NO:16), a stop codon and a human growth hormone terminator. The plasmid also has an *E. coli* origin of replication, a mammalian selectable marker expression unit having an SV40 promoter, enhancer and origin of replication, a DHFR gene and the SV40 terminator.

zSIG25NF/pZP9

A 490 bp PCR generated zSIG32/NF DNA fragment was created in accordance with the procedure set forth above using Z13446 (SEQ ID NO:25) and ZC13449 (SEQ ID NO:26) as PCR primers. The purified PCR fragment was digested with the restriction enzymes Bam HI (Boehringer Mannheim) and Xho I (Gibco BRL), followed by phenol/chloroform/isoamyl alcohol extraction and ETOH/glycogen precipitation.

The excised and restriction digested zSIG32 DNA was subcloned into plasmid NF/pZP9 which had been cut with Bam HI and Xba I. The zSIG32/NFpZP9 expression vector incorporates the TPA leader and attaches the FLAG tag (SEQ ID NO:16) to the N-terminal of the zsig25 polypeptide-encoding polynucleotide sequence. Plasmid NF/pZP9 (deposited at the American Type Culture Collection, 12301 Parklawn Drive, Rockville, Md.) is a mammalian expression vector containing an expression cassette having the mouse metallothionein-1 promoter, a TPA leader peptide followed by the sequence encoding the FLAG tag (SEQ ID NO:16), multiple restriction sites for insertion of coding sequences, and a human growth hormone terminator. The plasmid also contains an *E. coli* origin of replication, a mammalian selectable marker expression unit having an SV40 promoter, enhancer and origin of replication, a DHFR gene and the SV40 terminator.

For the untagged zsig32 construct 100 ng of the zsig32 insert and 90 ng of the Eco RI/Not I digested pZP9 vector were ligated as described for the tagged constructs. For the N- and C-tagged constructs, 10 ng of the restriction digested inserts and 20 ng of the corresponding vectors were ligated at room temperature for 4 hours. One microliter of each ligation reaction was independently electroporated into DH10B competent cells (GIBCO BRL, Gaithersburg, Md.) according to manufacturer's direction and plated onto LB plates containing 50 mg/ml ampicillin, and incubated overnight. Colonies were screened by PCR as described above. For zsig32/pZP9 screens the primers were ZC6583 (SEQ ID NO:27) and ZC5020 (SEQ ID NO:28), for zSIG32CF/pZP9 screens the primers were, ZC13465 (SEQ ID NO:23) and ZC13447 (SEQ ID NO:24) and for zSIG32NF/pZP9 screens the primers were ZC13448 (SEQ ID NO:25) and ZC13449 (SEQ ID NO:26). The insert sequence of positive clones, 1000 bp for zsig32 untagged, 490 bp fragment for zSIG32NF and a 553 bp fragment for zSIG32/CF were verified by sequence analysis. A large scale plasmid preparation was done using a QIAGEN® Maxi prep kit (Qiagen) according to manufacturer's instructions.

Example 5

Mammalian Expression of zsig32

BHK 570 cells (ATCC NO: CRL-10314) were plated in 10 cm tissue culture dishes and allowed to grow to approximately 50 to 70% confluency overnight at 37° C., 5% $CO_2$, in DMEM/FBS media (DMEM, Gibco/BRL High Glucose, (Gibco BRL, Gaithersburg, Md.), 5% fetal bovine serum (Hyclone, Logan, Utah), 1 $\mu$M L-glutamine (JRH Biosciences, Lenexa, Kans.), 1 $\mu$M sodium pyruvate (Gibco BRL)). The cells were then transfected with the plasmid zsig32NF/pZP9 (N-terminal FLAG tag), zsig32CF/pZP9 (C-terminal FLAG tag), or zsig32/pZP9 (untagged), using Lipofectamine™ (Gibco BRL), in serum free (SF) media formulation (DMEM, 10 mg/ml transferrin, 5 mg/ml insulin, 2 mg/ml fetuin, 1% L-glutamine and 1% sodium pyruvate). Sixteen micrograms of zsig32NF/pZP9 and 16 $\mu$g of zsig32CF/pZP9 were separately diluted into 15 ml tubes to a total final volume of 640 $\mu$l with SF media. In separate tubes, 35 $\mu$l of Lipofectamine™ (Gibco BRL) was mixed with 605 $\mu$l of SF medium. The Lipofectamine™ mix was added to the DNA mix and allowed to incubate approximately 30 minutes at room temperature. Five milliliters of SF media was added to the DNA:Lipofectamine™ mixture. Three plates of cells were rinsed once with 5 ml of SF media, aspirated, and the DNA:Lipofectamine™ mixture was added. The cells were incubated at 37° C. for five hours, then 6.4 ml of DMEM/10% FBS, 1% PSN media was added to each plate. The plates were incubated at 37° C. overnight and the DNA:Lipofectamine™ mixture was replaced with fresh FBS/DMEM media the next day. On day 2 post-transfection, the cells were split into the selection media (DMEM/FBS media from above with the addition of 1 $\mu$M methotrexate (Sigma Chemical Co., St. Louis, Mo.)) in 150 mm plates at 1:10, 1:20 and 1:50. The cells were refed at day 5 post-transfection with fresh selection media. Approximately 12 days post-transfection, two 150 mm culture dishes of methotrexate resistant colonies from each transfection were trypsinized and the cells were pooled and plated into a T-162 flask and transferred to large scale culture.

Example 6

Large Scale Mammalian Expression of zsig32

One T-162 flask, containing confluent cells expressing zsig32/NF and one flask containing zsig32/CF expressing cells, obtained from the expression procedure described above, were expanded into five T-162 flasks. One of the five resulting flasks was used to freeze down four cryovials, and the other four flasks were used to generate a Nunc cell factory.

The cells from the four T-165 flasks of zsig32/NF and zsig32/CF were combined and used to seed two Nunc cell factories (10 layers, commercially available from VWR). Briefly, the cells from the T-162 flasks described above were detached using trypsin, pooled, and added to 1.5 liters ESTEP1 media (668.7 g/50 L DMEM (Gibco), 5.5 g/50 L pyruvic acid, sodium salt 96i (Mallinckrodt), 185.0 g/50 L $NaHCO_3$ (Mallinkrodt), 5.0 mg/ml and 25 ml/50 L insulin (JRH Biosciences), 10.0 mg/ml and 25 ml/50 L transferrin (JRH Biosciences), 2.5 L/50 L fetal bovine serum (characterized) (Hyclone), 1 μM MTX, with pH adjusted to 7.05+/−0.05) prewarmed to 37° C. The media containing the cells was then poured into the Nunc cell factories via a funnel. The cell factories were placed in a 37° C./5.0% CO2 incubator.

At 80–103% confluence, a visual contamination test (phenol red color change) was performed on the Nunc cell factories. Since no contamination was observed, supernatant from the confluent factories was poured into a small harvest container, sampled and discarded. The adherent cells were then washed once with 400 ml PBS. To detach the cells from the factories, 100 mls of trypsin was added to each and removed and the cells were then incubated for 5 to 10 minutes in the residual trypsin. The cells were collected following two, 200 ml washes of ESTER1 media. To each of ten ESTEP1 media-containing bottles (1.5 liters each, at 37° C.) was added 40 mls of collected cells. One 1.5 liter bottle was then used to fill one Nunc factory. Each cell factory was placed in a 37° C./5.0% $CO_2$ incubator.

At 80–90% confluence, a visual contamination test (phenol red color change) was performed on the Nunc cell factories. Since no contamination was observed, supernatant from the confluent factories was poured into a small harvest container, sampled and discarded. Cells were then washed once with 400 ml PBS. 1.5 liters of ESTEP2 media (668.7 g/50 L DMEM (Gibco), 5.5 g/50 L pyruvic acid, sodium salt 96% (Mallinckrodt), 185.0 g/50 L $NaHCO_3$ (Mallinkrodt), 5.0 mg/ml, 25 ml/50 L insulin, 10.0 mg/ml and 25 ml/50 L transferrin) was added to each Nunc cell factory. The cell factories were incubated at 37° C./5.0% $CO_2$.

At approximately 48 hours a visual contamination test (phenol red color change) was performed on the Nunc cell factories. Supernatant from each factory was poured into small harvest containers. A total of 13.5 liters was collected from all 10 factories. Fresh serum-free media (1.5 liters) was poured into each Nunc cell factory, and the factories were incubated at 37° C./5.0% $CO_2$. One ml of supernatant harvest was transferred to a microscope slide, and subjected to microscopic analysis for contamination. The contents of the small harvest containers for each factory were pooled and immediately filtered. A second harvest was then performed, substantially as described above at 44 hours (13.5 L were obtained) and the cell factories were discarded thereafter. An aseptically assembled filter train apparatus was used for aseptic filtration of the harvest supernatant (conditioned media). Assembly was a follows: tubing was wire-tied to an Opti-Cap filter (Millipore Corp., Bedford, Mass.) and a Gelman Supercap 50 filter (Gelman Sciences, Ann Arbor, Mich.). The Supercap 50 filter was also attached to a sterile capped container located in a hood; tubing located upstream of the Millipore Opti-cap filter was inserted into a peristaltic pump; and the free end of the tubing was placed in the large harvest container. The peristaltic pump was run between 200 and 300 rpm, until all of the conditioned media passed through the 0.22 μm final filter into a sterile collection container. The filtrate was placed in a 4° C. cold room pending purification. The media was concentrated 10× with a Millipore 5 kDA cut off concentrator (Millipore Corp., Bedford, Mass.) according to manufacturer's direction and subjected to Western Blot analysis using an anti-FLAG tag antibody (Kodak).

Example 7

Purification of Mammalian Expressed FLAG-tagged zsig32 Polypeptides

Unless otherwise noted, all operations were carried out at 4° C. The following procedure was used to purify zsig32 constructs having an N-terminal or C-terminal flag tag. Protein was purified from the culture medium of a mixture of baby hamster kidney cell (BHK) clones that produced the N- or C-terminal tagged protein (zsig32NF and zsig32CF). A total of 25 liters of conditioned media from BHK cells was sequentially sterile filtered through a 4 inch, 0.2 mM Millipore (Bedford, Mass.) OptiCap capsule filter and a 0.2 mM Gelman (Ann Arbor, Mich.) Supercap 50. The material was then concentrated to about 1.3 liters using an Amicon (Beverly, Mass.) DC 10 L concentrator fitted with an A/G Tech (Needham, Mass.) hollow fiber cartridge with a 15 sq. ft. 3000 kDa cutoff membrane. The concentrated material was again sterile-filtered with the Gelman filter as described above. A 25.0 ml sample of anti-Flag Sepharose (Eastman Kodak, Rochester, N.Y.) was added to the sample for batch adsorption and the mixture was gently agitated on a Wheaton (Millville, N.J.) roller culture apparatus for 18.0 h at 4° C.

The mixture was then poured into a 5.0×20.0 cm Econo-Column (Bio-Rad, Laboratories, Hercules, Calif.) and the gel was washed with 30 column volumes of phosphate buffered saline (PBS). The unretained flow-through fraction was discarded. Once the absorbance of the effluent at 280 nM was less than 0.05, flow through the column was reduced to zero and the anti-Flag Sepharose gel was washed with 2.0 column volumes of PBS containing 0.2 mg/ml of Flag peptide, N-Asp-Tyr-Lys-Asp-Asp-Asp-Asp-Lys-C (SEQ ID NO:16) (Eastman Kodak). After 1.0 hour at 4° C., flow was resumed and the eluted protein was collected. This fraction is referred to as the peptide elution. The anti-Flag Sepharose gel was washed with 2.0 column volumes of 0.1M glycine, pH 2.5, and the glycine wash was collected separately. The pH of the glycine-eluted fraction was adjusted to 7.0 by the addition of a small volume of 10× PBS and stored at 4° C. for future analysis if needed.

The peptide elution was concentrated to 5.0 ml using a 5,000 molecular weight cutoff membrane concentrator (Millipore, Bedford, Mass.) according to the manufacturer's instructions. The concentrated peptide elution was then separated from free peptide by chromatography on a 1.5×50 cm Sephadex G-50 (Pharmacia, Piscataway, N.J.) column equilibrated in PBS at a flow rate of 1.0 ml/min using a BioCad Sprint HPLC system (PerSeptive BioSystems, Framingham, Mass.). Two-ml fractions were collected and the absorbance at 280 nM was monitored. The first peak of material absorbing at 280 nM and eluting near the void volume of the column was collected.

By SDS-PAGE and Western analysis with anti-Flag M2 antibodies (Kodak) the purified zsig32 NF/CF preparation was composed of one major Coomassie Blue-stained band of apparent molecular weight 25,000. Two minor bands of apparent molecular weights 22,000 and 27,000, were also observed on the Coomassie Blue-stained gel. All three bands showed cross-reactivity with the anti-Flag M2 antibody on Western blots. Migration of the proteins on SDS-PAGE gels and Western blots was not changed by reducing agents.

The protein concentration of the purified proteins (0.67 mg/ml) was determined by BCA analysis (Pierce, Rockford, Ill.) and the material was aliquoted, and stored at −80° C.

Example 8

Creation of Baculovirus Expression Vectors pFSG32, pFSGE32, pSSGE32 and pLSGE32

Four expression vectors were prepared to express zsig32 polypeptides in insect cells: pFSG32, designed to express an untagged zsig32 polypeptide; and pFSGE32, pSSGE32 and pLSGE32, designed to express a zsig32 polypeptide with a C-terminal Glu—Glu tag (SEQ ID NO:12).

pFSG32

A 559 bp PCR generated zsig32 DNA fragment was created using ZC13404 (SEQ ID NO:13) and ZC13409 (SEQ ID NO:14) as PCR primers and zsig32/pZP9, described above, as a template. The PCR reaction was incubated at 94° C. for 2 minutes, followed by 30 cycles of 45 seconds at 94° C., 1 minute at 60° C. and 72° C. for 1 minute with a 1 second/cycle segment extension. The resultant PCR product was then run on a 3% gel (2% NuSieve/1% BRL agarose). The 559 bp fragment was captured by diluting 15 fold with 0.1 mM EDTA pH 8.0 and then ligated into the vector pCR2.1 (TA Cloning Kit, Invitrogen Inc., San Diego, Calif.) according to manufacturer's instructions. The resultant clones were screened for the proper insert orientation and sequenced to confirm identify. The resulting clone, designated pSG32a, was digested with Bam HI and Asp718 and the digest run on a 1% SeaPlaque/1% NuSieve agarose gel. The band was excised, diluted to 0.5% agarose with 2 mM $MgCl_2$, melted at 65° C. and ligated into a Bam HI/Asp718 digested baculovirus expression vector, pFast-Bacl (Bac-to-Bac™ System, GIBCO-BRL, Gaithersburg, Md.). Forty four nanograms of the restriction digested zsig32 insert and 126 ng of the corresponding vector were ligated overnight. The ligation mix was diluted 3 fold in TE (10 mM Tris-HCl, pH 7.5 and 1 mM EDTA) and 4 fmol of the diluted ligation mix was transformed into DH5α Library Efficiency competent cells (Life Technologies) according to manufacturer's direction by heat shock for 45 seconds in a 42° C. waterbath. The ligated DNA was diluted in 450 µl SOC media (2% Bacto Tryptone, 0.5% Bacto Yeast Extract, 10 ml 1M NaCl, 1.5 mM KCl, 10 mM $MgCl_2$, 10 mM $MgSO_4$ and 20 mM glucose) and plated onto LB plates containing 100 µg/ml ampicillin. The plates were incubated overnight at 37° C. Plasmid DNA was prepared using the QiaVac Miniprep8 system (Qiagen) according the manufacturer's directions. The clones were screened by restriction digest with Hind III/BspE1.

pFSGE32

A zsig32 fragment having a C-terminal Glu—Glu tag (SEQ ID NO:12) was generated by PCR as described above using oligonucleotide primers ZC13404 (SEQ ID NO:13) and ZC13407 (SEQ ID NO:15). A fragment of the expected size, 580 bp, was detected by gel electrophoresis. The DNA fragment was digested with the restriction enzymes Bam HI and Asp718 and the resulting 565 bp zsig32 restriction fragment was ligated into a Bam HI/Asp718 digested pFast-Bacl vector and transformed into DH10α cells as described above.

pSSGE32 and pLSGE32

A 580 bp zsig32 fragment having a C-terminal Glu—Glu tag (SEQ ID NO:12) was generated by PCR as described above. The fragment was visualized by gel electrophoresis, restriction digested and ligated into the expression vectors, pFBPL2 and pFBPS2, as described above. The vectors, pFBPL2 and pFBPS2, were derived from a modified pFast-Bacl™ vector. The polyhedrin promoter was removed and substituted with a short (FBPS) or long (FBPL) version of the baculovirus basic protein promoter as is known in the art (Hill-Perkins and Possee, ibid.; Bonning et al., ibid.; and, Chazenbalk and Rapoport, ibid.).

One microliter of each of the above constructs was used to independently transform 20 µl DH10Bac Max Efficiency competent cells (GIBCO-BRL, Gaithersburg, Md.) according to manufacturer's instruction, by heat shock at 42° C. for 45 seconds. The transformants were then diluted in an appropriate volume of SOC media and plated on to Luria Agar plates containing 50 µg/ml kanamycin, 7 µg/ml gentamicin, 10 µg/ml tetracycline, IPTG and Bluo Gal. The cells were incubated for 48 hours at 37° C. A color selection was used to identify those cells having virus that had incorporated into the plasmid (referred to as a "bacmid"). Those colonies, which were white in color, were picked for analysis. Bacmid DNA was isolated from positive colonies and screened for the correct insert using PCR. Oligonucleotide primers ZC976 (SEQ ID NO:17) and ZC447 (SEQ ID NO:18) were used and those having the correct insert were used to transfect Spodoptera frugiperda (Sf9) cells.

Sf9 cells were seeded at $5 \times 10^6$ cells per 35 mm plate and allowed to attach for 1 hour at 27° C. Five microliters of bacmid DNA was diluted with 100 µl Sf-900 II SFM. Six to 10 µl of CellFECTIN Reagent (Life Technologies) was diluted with 100 µl Sf-900 II SMF. The bacmid DNA and lipid solutions were gently mixed and incubated 30–45 minutes at room temperature. The media from one plate of cells were aspirated, and the lipid-DNA mixture to which 0.8 ml of Sf-900 II SFM was added. The cells were incubated at 27° C. for 4–5 hours, then 2 ml of Sf-900 II media containing penicillin/streptomycin was added to each plate. The plates were incubated at 27° C., 90% humidity, for 72 hours after which the virus was harvested.

Primary Amplification

Sf9 cells were grown in 50 ml Sf-900 II SFM in a 50 ml shake flask to an approximate density of $0.04$–$0.50 \times 10^6$ cells/ml. They were then transfected with 50–1000 µl of the virus stock from above and incubated at 27° C. for 3–5 days after which time the virus was harvested, titer $0.53 \times 10^8$ pfu/ml. To scale up, $1.5 \times 10^6$ SF9 cells/ml were added to five liters of SF 900 II SFM and grown for 91 hours. The cells were then transfected with the harvested virus (MOI 0.2) and incubated as above for 71 hours.

Example 9

Purification of Baculovirus Expressed Glu—Glu-tagged zsig32 Polypeptides

Unless otherwise noted, all operations were carried out at 4° C. A mixture of protease inhibitors were added to a 2 liter sample of conditioned media from C-terminal Glu—Glu (EE) tagged zsig32 baculovirus-infected Sf9 cells to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim). The sample was centrifuged at 10,000 rpm for 30 min at 4° C. in a Beckman JLA-10.5 rotor (Beckman Instruments) in a Beckman Avanti J25I centrifuge (Beckman Instruments) to remove cell debris. To the supernatant fraction was added a 50.0 ml sample of anti-EE Sepharose, prepared as described below, arid the mixture was gently agitated on a Wheaton (Millville, N.J.) roller culture apparatus for 18.0 h at 4° C.

The mixture was poured into a 5.0×20.0 cm Econo-Column (Bio-Rad Laboratories) and the gel was washed with 30 column volumes of phosphate buffered saline (PBS). The unretained flow-through fraction was discarded. Once the absorbance of the effluent at 280 nM was less than 0.05, flow through the column was reduced to zero and the anti-EE Sepharose gel was washed with 2.0 column volumes of PBS containing 0.2 mg/ml of EE peptide (AnaSpec, San Jose, Calif.). The peptide used has the sequence Glu-Tyr-Met-Pro-Val-Asp (SEQ ID NO: 19). After 1.0 hour at 4° C., flow was resumed and the eluted protein was collected. This fraction was referred to as the peptide elution. The anti-EE Sepharose gel was washed with 2.0 column volumes of 0.1 M glycine, pH 2.5, and the glycine wash was collected separately. The pH of the glycine-eluted fraction was adjusted to 7.0 by the addition of a small volume of 10× PBS and stored at 4° C.

The peptide elution was concentrated to 5.0 ml using a 5,000 molecular weight cutoff membrane concentrator (Millipore) according to the manufacturer's instructions. The concentrated peptide elution was separated from free peptide by chromatography on a 1.5×50 cm Sephadex G-50 (Pharmacia) column equilibrated in PBS at a flow rate of 1.0 ml/min using a BioCad Sprint HPLC (PerSeptive BioSystems). Two ml fractions were collected and the absorbance at 280 nM was monitored. The first peak of material absorbing at 280 nM and eluting near the void volume of the column was collected. This material represented purified zsig32CEE and was composed of two major bands of apparent molecular weights 19,000 and 24,000 on Coomassie Blue-stained SDS-PAGE gels. These bands were present in about equimolar amounts. Both bands showed cross-reactivity with anti-EE antibodies by Western blotting of the purified material. The protein concentration (0.53 mg/ml) of the purified proteins was determined by BCA analysis (Pierce) and the material was aliquoted, and stored at −80° C.

Preparation of anti-EE Sepharose

A 100 ml bed volume of protein G-Sepharose (Pharmacia) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2 HCl (Pierce), dissolved in TEA, was added to a final concentration of 36 mg/ml of gel. The gel was rocked at room temperature for 45 min and the liquid was removed using the filter unit as described above. Nonspecific sites on the gel were then blocked by incubating for 10 minutes at room temperature with 5 volumes of 20 mM ethanolamine in 200 mM TEA. The gel was then washed with 5 volumes of PBS containing 0.02% sodium azide and stored in this solution at 4° C.

Example 9

Construction of zsig32 Amino Terminal FLAG-Tagged Pichia Expression Vector

Expression of zsig32 in *Pichia methanolica* utilizes the expression system described in co-assigned WIPO publication WO 97/17450. An expression plasmid containing all or part of a polynucleotide encoding zsig32 was constructed via homologous recombination. The expression vector was built from pCZR190, which contains the AUG1 promoter, followed by the alpha factor prepro (αFpp) leader sequence, followed by an amino-terminal FLAG tag (NF), a blunt-ended Sma I restriction site for insertion of the gene sequence of interest, a translational stop codon, followed by the AUG1 terminator, the ADE2 selectable marker, and finally the AUG1 3' untranslated region. Also included in this vector are the URA3 and CEN-ARS sequences required for selection and replication in *S. cerevisiae*, and the AmpR and colE1 ori sequences required for selection and replication in *E. coli*. The zsig32 sequence inserted into this vector begins at residue 22 (Ala) of the zsig32 amino acid sequence (SEQ ID NO:2).

Two construct specific linkers were prepared and along with zsig32, were homologously recombined into the yeast expression vector pCZR190. The N-terminal linker comprises 70 base pairs of the αFpp coding sequence joined to a nucleotide sequence encoding a FLAG tag (SEQ ID NO:16) followed by 70 base pairs of nucleotide sequence encoding a portion of the amino-terminus from the mature zsig32 sequence. The C-terminal linker comprises about 70 base pairs of carboxy terminus coding sequence of the zsig32 joined with 70 base pairs of AUG1 terminator sequence.

The N-terminal linker was synthesized by a PCR reaction. Briefly, to a final reaction volume of 100 μl was added 1 pm each of each linker ZC13735 (SEQ ID NO:29), ZC14291 (SEQ ID NO:30), and 100 pmol of each primer ZC13497 (SEQ ID NO:31) and ZC14279 (SEQ ID NO:32), 10 μl of 10× PCR buffer (Boehringer Mannheim), 1 μl Two polymerase (Boehringer Mannheim), 10 μl of 0.25 mM nucleotide triphosphate mix (Perkin Elmer) and dH$_2$O. The PCR reaction was incubated at 94° C. for 1.5 minutes, followed by 10 cycles of 30 seconds at 94° C., 1 minute at 50° C. and 1 minute at 72° C., concluded with a 10 minute extension at 72°. The resulting 138 bp double stranded, NF-tagged linker is disclosed in SEQ ID NO:33.

The C-terminal untagged zsig32 linker was made via a PCR reaction as described using oligonucleotides linkers ZC14346 (SEQ ID NO:34) and ZC14218 (SEQ ID NO:35) and primers ZC14278 (SEQ ID NO:36) and ZC13734 (SEQ ID NO:37). The resulting 153 bp double stranded, C-terminal untagged linker is disclosed in SEQ ID NO:38.

The NF-zsig32 plasmid was made by homologously recombining 100 ng of Sma I digested pCZR202 acceptor vector, the 1 μg of Eco RI-Xho I zsig32 cDNA donor fragment, 1 μg of N-terminal FLAG-tagged zsig32 linker (SEQ ID NO:33) and 1 μg of C-terminal linker (SEQ ID NO:38) into *S. cerevisiae*. One hundred microliters of competent yeast cells (*S. cerevisiae*) was combined with 10 μl of each of the fragments and linkers and transferred to a 0.2 cm electroporation cuvette. The yeast/DNA mixture was electropulsed at 0.75 kV (5 kV/cm), ∞ ohms, 25 μF. To the cuvette was added 600 μl of 1.2 M sorbitol and 300 μl aliquots of the yeast/sorbitol mixture was plated onto two URA D plates and incubated at 30° C.

After about 48 hours the Ura$^+$ yeast transformants from a single plate were resuspended in 2.5 ml H$_2$O and spun briefly to pellet: the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase was transferred to a fresh tube and the DNA precipitated with 600 μl ethanol (EtOH), followed by a 10 minutes at 4° C. The DNA pellet was resuspended in 100 μl H$_2$O.

Five microliters of the resuspended DNA prep was used to transform 40 μl of electrocompetent *E. coli* cells (DH10B, Gibco BRL). The cells were electropulsed at 2.0 kV and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was added and the cells were allowed to recover for 1 hour at 37° C. prior to plating 250 µl aliquots on four LB AMP plates (LB broth (Lennox), 1.8% Bacto™ Agar (Difco), 100 mg/L Ampicillin).

Individual clones harboring the correct expression construct were identified by PCR screening. The primers used to amplify the N-tagged zsig32 clone were ZC13479 (SEQ ID NO:31) and ZC13734 (SEQ ID NO:37). The insert sequence of positive clones, identified by a 625 bp fragment, were verified by sequence analysis. One such clone was designated pGMN12-1. Larger scale plasmid DNA was isolated using Qiagen maxi kits (Qiagen) and the DNA was digested with Not I to liberate the Pichia-zsig32 expression cassette from the vector backbone. The Not I DNA fragment was then transformed into the *Pichia methanolica* expression host, PMAD16. This was done by mixing 100 µl of prepared competent PMAD16 cells with 10 µg of Not I digested NF-tagged zsig32 fragment and transferred to a 0.2 cm electroporation cuvette. The yeast/DNA mixture was electropulsed at 0.75 kV, 25 pF, infinite ohms. To the cuvette was added 1 ml of 1× Yeast Nitrogen Base and 500 µl aliquots were plated onto two ADE DS (0.056% -Ade -Trp -Thr powder, 0.67% yeast nitrogen base without amino acids, 2% D-glucose, 0.5% 200× tryptophan, threonine solution, and 18.22% D-sorbitol) plates for selection and incubated at 30° C. The resulting NF-tagged-zsig32 plasmid was designated PMAD16::pGMN12-1. Transformants were then picked and screened via Western blot for high-level NF-tagged zsig32 expression and subjected to large scale fermentation.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An expression vector comprising the following operably linked elements:
   a transcription promoter;
   a DNA segment encoding a polypeptide comprising a sequence of amino acid residues that is at least 80% identical in amino acid sequence to residues 23–178 of SEQ ID NO:2; and
   a transcriptional terminator.

2. An expression vector according to claim 1, wherein said DNA segment encodes a polypeptide is at least 90% identical in amino acid sequence to residues 23–178 of SEQ ID NO:2.

3. An expression vector according to claim 1, wherein said polypeptide encoded by said DNA segment comprises residues 27–178 of SEQ ID NO:2.

4. An expression vector according to claim 1, wherein said polypeptide encoded by said DNA segment comprises residues 7–178 of SEQ ID NO:2.

5. An expression vector according to claim 1, wherein said polypeptide encoded by said DNA segment comprises residues 1–178 of SEQ ID NO:2.

6. An expression vector according to claim 1, wherein said DNA segment encodes a polypeptide covalently linked to an affinity tag selected from the group consisting of polyhistidine, FLAG, Glu—Glu, glutathione S transferase, and an immunoglobulin heavy chain constant region.

7. An expression vector according to claim 1 wherein said DNA further encodes a secretory signal sequence operably linked to said polypeptide.

8. An expression vector according the claim 7, wherein said secretory signal sequence encodes residues 7–22 of SEQ ID NO:2.

9. An expression vector according the claim 7, wherein said secretory signal sequence encodes residues 1–22 of SEQ ID NO:2.

10. A cultured cell into which has been introduced an expression vector according to claim 1, wherein said cell expresses said polypeptide encoded by said DNA segment.

11. A method of producing a protein comprising:
   culturing a cell into which has been introduced an expression vector according to claim 1 whereby said cell expresses said protein encoded by said DNA segment; and
   recovering said expressed protein.

12. An isolated polynucleotide encoding a polypeptide comprising a sequence of amino acid residues that is at least 80% identical in amino acid sequence to residues 23–178 of SEQ ID NO:2.

13. An isolated polynucleotide according to claim 12, wherein said polypeptide is at least 90% identical in amino acid sequence to residues 23–178 of SEQ ID NO:2.

14. An isolated polynucleotide according to claim 12, wherein said polypeptide comprises residues 7–178 of SEQ ID NO:2.

15. An isolated polynucleotide according to claim 12, wherein said polypeptide comprises residues 1–178 of SEQ ID NO:2.

16. An isolated polynucleotide according to claim 12, wherein said polynucleotide is selected from the group consisting of,
   a) a sequence of nucleotides from nucleotide 168 to nucleotide 704 of SEQ ID No:1;
   c) a sequence of nucleotides from nucleotide 234 to nucleotide 704 of SEQ ID NO: 1;
   d) a sequence of nucleotides from nucleotide 246 to nucleotide 704 of SEQ ID NO: 1; and f) nucleotide sequences complementary to a), b), c), or d).

17. An isolated polynucleotide according to claim 12, wherein said polynucleotide is approximately 1 kb in length.

18. An isolated polynucleotide according to claim 12, wherein said polynucleotide is from 471 to 853 nucleotides in length.

19. An isolated polynucleotide according to claim 12 comprising nucleotide 1 to nucleotide 534 of SEQ ID NO:20.

20. An isolated polynucleotide according to claim 12, wherein said polynucleotide is DNA.

* * * * *

```
                         SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
        (A) LENGTH: 853 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 168...701
        (D) OTHER INFORMATION:

(xi) SEQUENCE DESCRIPTION: SEQ ID NO:1:

GAATTCGGCT CGAGAGGAAG AGCCCCACGG CCAGCTCCTT CCTGTTCCCC TGGCGGCCCC         60

TCGCTTCTTC CTTCTGGATG GGGGCCCAGG GGGCCCAGGA GAGTATAAAG GCGATGTGGA        120

GGGTGCCCGG CACAACCAGA CGCCCAGTCA CAGGCGAGAG CCCTGGG ATG CAC CGG          176
                                                  Met His Arg
                                                    1

CCA GAG GCC ATG CTG CTG CTG CTC ACG CTT GCC CTC CTG GGG GGC CCC          224
Pro Glu Ala Met Leu Leu Leu Leu Thr Leu Ala Leu Leu Gly Gly Pro
      5                  10                  15

ACC TGG GCA GGG AAG ATG TAT GGC CCT GGA GGA GGC AAG TAT TTC AGC          272
Thr Trp Ala Gly Lys Met Tyr Gly Pro Gly Gly Gly Lys Tyr Phe Ser
 20                  25                  30                  35

ACC ACT GAA GAC TAC GAC CAT GAA ATC ACA GGG CTG CGG GTG TCT GTA          320
Thr Thr Glu Asp Tyr Asp His Glu Ile Thr Gly Leu Arg Val Ser Val
                 40                  45                  50

GGT CTT CTC CTG GTG AAA AGT GTC CAG GTG AAA CTT GGA GAC TCC TGG          368
Gly Leu Leu Leu Val Lys Ser Val Gln Val Lys Leu Gly Asp Ser Trp
             55                  60                  65

GAC GTG AAA CTG GGA GCC TTA GGT GGG AAT ACC CAG GAA GTC ACC CTG          416
Asp Val Lys Leu Gly Ala Leu Gly Gly Asn Thr Gln Glu Val Thr Leu
         70                  75                  80

CAG CCA GGC GAA TAC ATC ACA AAA GTC TTT GTC GCC TTC CAA GCT TTC          464
```

-continued

```
Gln Pro Gly Glu Tyr Ile Thr Lys Val Phe Val Ala Phe Gln Ala Phe
        85                  90                  95

CTC CGG GGT ATG GTC ATG TAC ACC AGC AAG GAC CGC TAT TTC TAT TTT        512
Leu Arg Gly Met Val Met Tyr Thr Ser Lys Asp Arg Tyr Phe Tyr Phe
100                 105                 110                 115

GGG AAG CTT GAT GGC CAG ATC TCC TCT GCC TAC CCC AGC CAA GAG GGG        560
Gly Lys Leu Asp Gly Gln Ile Ser Ser Ala Tyr Pro Ser Gln Glu Gly
                120                 125                 130

CAG GTG CTG GTG GGC ATC TAT GGC CAG TAT CAA CTC CTT GGC ATC AAG        608
Gln Val Leu Val Gly Ile Tyr Gly Gln Tyr Gln Leu Leu Gly Ile Lys
            135                 140                 145

AGC ATT GGC TTT GAA TGG AAT TAT CCA CTA GAG GAG CCG ACC ACT GAG        656
Ser Ile Gly Phe Glu Trp Asn Tyr Pro Leu Glu Glu Pro Thr Thr Glu
        150                 155                 160

CCA CCA GTT AAT CTC ACA TAC TCA GCA AAC TCA CCC GTG GGT CGC TAGGG      706
Pro Pro Val Asn Leu Thr Tyr Ser Ala Asn Ser Pro Val Gly Arg
165                 170                 175

TGGGGTATGG GGCCATCCGA GCTGAGGCCA TCTGTGTGGT GGTGGCTGAT GGTACTGGAG      766

TAACTGAGTC GGGACGCTGA ATCTGAATCC ACCAATAAAT AAAGCTTCTG CAGAATCAGT      826

GAAAAAAAAA AAAAAAGGG CGGCCGC                                           853
```

(2) INFORMATION FOR SEQ ID NO:2:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met His Arg Pro Glu Ala Met Leu Leu Leu Thr Leu Ala Leu Leu
1               5                   10                  15

Gly Gly Pro Thr Trp Ala Gly Lys Met Tyr Gly Pro Gly Gly Lys
                20                  25                  30

Tyr Phe Ser Thr Thr Glu Asp Tyr Asp His Glu Ile Thr Gly Leu Arg
        35                  40                  45

Val Ser Val Gly Leu Leu Leu Val Lys Ser Val Gln Val Lys Leu Gly
50                  55                  60

Asp Ser Trp Asp Val Lys Leu Gly Ala Leu Gly Gly Asn Thr Gln Glu
65                  70                  75                  80

Val Thr Leu Gln Pro Gly Glu Tyr Ile Thr Lys Val Phe Val Ala Phe
                85                  90                  95

Gln Ala Phe Leu Arg Gly Met Val Met Tyr Thr Ser Lys Asp Arg Tyr
            100                 105                 110

Phe Tyr Phe Gly Lys Leu Asp Gly Gln Ile Ser Ser Ala Tyr Pro Ser
        115                 120                 125

Gln Glu Gly Gln Val Leu Val Gly Ile Tyr Gly Gln Tyr Gln Leu Leu
    130                 135                 140

Gly Ile Lys Ser Ile Gly Phe Glu Trp Asn Tyr Pro Leu Glu Glu Pro
145                 150                 155                 160

Thr Thr Glu Pro Pro Val Asn Leu Thr Tyr Ser Ala Asn Ser Pro Val
                165                 170                 175

Gly Arg
```

(2) INFORMATION FOR SEQ ID NO:3:

(i) SEQUENCE CHARACTERISTICS:
        (A) LENGTH: 199 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Met Leu Leu Leu Thr Leu Ala Phe Leu Ala Ser Pro Thr Cys Arg
 1               5                  10                  15

Ala Gln Asn Val Leu Gly Asn Ala Ala Gly Lys Tyr Phe Tyr Val Gln
            20                  25                  30

Gly Glu Asp Gln Gly Gln Leu Lys Gly Met Arg Ile Phe Leu Ser Val
            35                  40                  45

Phe Lys Phe Ile Lys Gly Phe Gln Leu Gln Phe Gly Ser Asn Trp Thr
 50                  55                  60

Asp Val Tyr Gly Thr Arg Ser Asp Asn Phe Ile Asp Phe Leu Leu Glu
65                   70                  75                  80

Asp Gly Glu His Val Ile Lys Val Glu Gly Ser Ala Val Ile Cys Leu
                 85                  90                  95 hr Ser Leu Thr Phe Thr Thr Asn Lys Gly Arg Val Ala Thr Phe Gly
            100                 105                 110

Val Arg Arg Gly Arg Tyr Phe Ser Asp Thr Gly Ser Asp Lys His
            115                 120                 125

Leu Val Thr Val Asn Gly Met His Ala Pro Gly Leu Cys Val Arg Gly
            130                 135                 140

Ile Gly Phe Lys Trp Gly Asn Ile Asn Ala Asn Gly Asn Asp His Tyr
145                 150                 155                 160

Asn Asn Lys Glu Asp Lys Ala Asp Asn Lys Asp Ala Asp Asn Lys Asp
                165                 170                 175

Ala Asp Asn Lys Asp Asp Gly Asp Glu Asp Asp Asp Gly Asn Asp Asp
            180                 185                 190

Asp Asp Gln Lys Asp Glu Ser
            195
```

(2) INFORMATION FOR SEQ ID NO:4:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Leu Pro Gln Leu Glu Ala Met Leu Pro Leu Ile Leu Ala Phe
 1               5                  10                  15

Leu Gly Thr Pro Ala Val Leu Thr Gln Ser Arg Tyr His Gly Ser Glu
            20                  25                  30

Thr Gly Lys His Phe Cys Ile Val Ala Pro Glu Gly Glu Pro Val Thr
            35                  40                  45

Gly Ile Trp Ala Ser Leu Lys Asn Asn Ile Leu Ser Ser Ile Arg Leu
 50                  55                  60

Lys Phe Gly Asn Asn Trp Ser Gln Glu Tyr Gly Ser Ser Gly Arg Ala
65                   70                  75                  80
```

```
Glu Ile Glu Val Lys Leu Asn Pro Asp Glu Thr Val Leu Gly Phe Ser
                85                  90                  95

Gly Ser Phe Tyr Ile Phe Met His Gln Ile Ile Thr Thr Ser Gln
            100                 105                 110

Pro Arg Glu Leu Ile Ile Gly Pro Leu Thr Gly Arg Tyr Val Tyr Thr
            115                 120                 125

Ser Tyr Pro Glu Asn Pro Asn His Val Phe Arg Gly Ile Cys Gly Tyr
            130                 135                 140

Tyr Val Thr Gly Gly Leu Lys Gly Met Arg Tyr Leu Trp Gly Asn Val
145                 150                 155                 160

Asn Gly Thr Cys Thr Glu
                165
```

(2) INFORMATION FOR SEQ ID NO:5:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Phe Gln Leu Glu Ala Met Leu Pro Leu Leu Ile Leu Ala Phe Leu
1                   5                   10                  15

Gly Thr Pro Thr Val Leu Thr Gln Asp Tyr His Gly Pro Glu Val Gly
            20                  25                  30

Lys His Ser Cys Thr Ser Ala Pro Glu Gly Lys Asn Ile Thr Ser Ile
            35                  40                  45

Arg Val Phe Leu Gln Gly Arg Ser Ile Val Gly Ile Gln Phe Asn Tyr
50                  55                  60

Asn Asn Glu Asp Gly Gln Val Tyr Gly Ser Thr Ala Gly Lys Val Met
65                  70                  75                  80

Val Ala Arg Leu Asn Asn Glu Glu Ser Ile Ile Ala Ala Glu Gly Thr
                85                  90                  95

Tyr Ser Pro Ser Ala Leu Thr Gln Ile Ile Phe Thr Thr Asn Gln Pro
            100                 105                 110

Arg Gln Leu Met Val Gly Tyr Tyr Val Gly Ser Ser Glu Tyr Ser Ser
            115                 120                 125

Phe Pro Asp Asp Pro Ser His Val Leu Lys Gly Ala Cys Val Ser Trp
            130                 135                 140

Arg Ala Gly Gly Ile Lys Ser Ile Leu Phe Leu Trp Gly Thr Glu Asn
145                 150                 155                 160

Ser Ser Cys Val Lys Tyr Gly His Ser Gly
            165                 170
```

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Leu Leu Thr Leu Ala Leu Leu Gly Gly Pro Thr Trp Ala Gly Lys
```

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC12493

(xi) SEQUENCE DESCRIPTION: SEQ ID NO:7:

GGTGCTGAAA TACTTGCCTC CTCCAGGGCC ATACATCTTC        40

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC694

(xi) SEQUENCE DESCRIPTION: SEQ ID NO:8:

TAATACGACT CACTATAGGG        20

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC695

(xi) SEQUENCE DESCRIPTION: SEQ ID NO:9:

GATTTAGGTG ACACTATAG        19

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13183

(xi) SEQUENCE DESCRIPTION: SEQ ID NO:10:

ATAGAAATAG CGGTCCTTGC        20

(2) INFORMATION FOR SEQ ID NO:11:

(i) SEQUENCE CHARACTERISTICS:
        (A) LENGTH: 20 base pairs

```
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC13187

(xi) SEQUENCE DESCRIPTION: SEQ ID NO:11:

GCAGCCAGGC GAATACATCA                                           20

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Glu Glu Tyr Met Pro Met Glu
1               5

(2) INFORMATION FOR SEQ ID NO:13:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC13404

(xi) SEQUENCE DESCRIPTION: SEQ ID NO:13:

GGCGAGAGGA TCCGCATGCA CCGGCCAGAG GCCATGCT                        38

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC13409

(xi) SEQUENCE DESCRIPTION: SEQ ID NO:14:

CCGGTACCTA GCGACCCACG GGTGAGTTTG CTGA                            34

(2) INFORMATION FOR SEQ ID NO:15:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC13407
```

(xi) SEQUENCE DESCRIPTION: SEQ ID NO:15:

CCGGTACCTA TTCCATCGGC ATGTATTCTT CGCGACCCAC GGGTGAGTTT GCTGA                55

(2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Asp Tyr Lys Asp Asp Asp Asp Lys
 1               5

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC976

(xi) SEQUENCE DESCRIPTION: SEQ ID NO:17:

CGTTGTAAAA CGACGGCC                                                         18

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC447

(xi) SEQUENCE DESCRIPTION: SEQ ID NO:18:

TAACAATTTC ACACAGG                                                          17

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Glu Tyr Met Pro Val Asp
 1               5

(2) INFORMATION FOR SEQ ID NO:20:

(i) SEQUENCE CHARACTERISTICS:
        (A) LENGTH: 534 base pairs
        (B) TYPE: nucleic acid
        (C) STRANDEDNESS: single (D) TOPOLOGY: linear (ii) MOLECULE TYPE: Other (xi) SEQUENCE DESCRIPTION: SEQ ID NO:20:

ATGCAYMGNC CNGARGCNAT GYTNYTNYTN YTNACNYTNG CNYTNYTNGG NGGNCCNACN      60

TGGGCNGGNA ARATGTAYGG NCCNGGNGGN GGNAARTAYT TYWSNACNAC NGARGAYTAY     120

GAYCAYGARA THACNGGNYT NMGNGTNWSN GTNGGNYTNY TNYTNGTNAA RWSNGTNCAR     180

GTNAARYTNG GNGAYWSNTG GGAYGTNAAR YTNGGNGCNY TNGGNGGNAA YACNCARGAR     240

GTNACNYTNC ARCCNGGNGA RTAYATHACN AARGTNTTYG TNGCNTTYCA RGCNTTYYTN     300

MGNGGNATGG TNATGTAYAC NWSNAARGAY MGNTAYTTYT AYTTYGGNAA RYTNGAYGGN     360

CARATHWSNW SNGCNTAYCC NWSNCARGAR GGNCARGTNY TNGTNGGNAT HTAYGGNCAR     420

TAYCARYTNY TNGGNATHAA RWSNATHGGN TTYGARTGGA AYTAYCCNYT NGARGARCCN     480

ACNACNGARC CNCCNGTNAA YYTNACNTAY WSNGCNAAYW SNCCNGTNGG NMGN           534

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
         (B) CLONE: ZC13703

(xi) SEQUENCE DESCRIPTION: SEQ ID NO:21:

CCTGGGACGT GAAACTGG                                                   18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
         (B) CLONE: ZC13704

(xi) SEQUENCE DESCRIPTION: SEQ ID NO:22:

TGGAAGGCGA CAAAGACT                                                   18

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
         (B) CLONE: ZC13465

(xi) SEQUENCE DESCRIPTION: SEQ ID NO:23:

GCGGGATCC GCGACCCACG GGTGA                                            25

-continued (2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC13447

(xi) SEQUENCE DESCRIPTION: SEQ ID NO:24:

GCGCGAATTC ATGCACCGGC CAGAG                                        25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC13448

(xi) SEQUENCE DESCRIPTION: SEQ ID NO:25:

CGCGCTCGAG CTAGCGACCC ACGGG                                        25

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC13449

(xi) SEQUENCE DESCRIPTION: SEQ ID NO:26:

GCGCGGATCC GGGAAGATGT ATGGC                                        25

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC6583

(xi) SEQUENCE DESCRIPTION: SEQ ID NO:27:

GTCCAACGAC TATAAAGAGG G                                                 21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
             (B) CLONE: ZC5020

(xi) SEQUENCE DESCRIPTION: SEQ ID NO:28:

CACTGGAGTG GCAACTTCCA G                                              21

(2) INFORMATION FOR SEQ ID NO:29:

(i) SEQUENCE CHARACTERISTICS:
             (A) LENGTH: 51 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (B) CLONE: ZC13735

(xi) SEQUENCE DESCRIPTION: SEQ ID NO:29:

GGTGTAAGCT TGGACAAGAG AGATTACAAG GACGATGATG ACAAGGGTGG T             51

(2) INFORMATION FOR SEQ ID NO:30:

(i) SEQUENCE CHARACTERISTICS:
             (A) LENGTH: 66 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (B) CLONE: ZC14291

(xi) SEQUENCE DESCRIPTION: SEQ ID NO:30:

TGGTGCTGAA ATACTTGCCT CCTCCAGGGC CATACATCTT CCCACCACCC TTGTCATCAT    60

CGTCCT                                                              66

(2) INFORMATION FOR SEQ ID NO:31:

(i) SEQUENCE CHARACTERISTICS:
             (A) LENGTH: 44 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (B) CLONE: ZC14297

(xi) SEQUENCE DESCRIPTION: SEQ ID NO:31:

AGCATTGCTG CTAAAGAAGA AGGTGTAAGC TTGGACAAGA GAGA                     44

(2) INFORMATION FOR SEQ ID NO:32:

(i) SEQUENCE CHARACTERISTICS:
             (A) LENGTH: 50 base pairs
             (B) TYPE: nucleic acid
             (C) STRANDEDNESS: single
             (D) TOPOLOGY: linear (ii) MOLECULE TYPE: cDNA (vii) IMMEDIATE SOURCE:
             (B) CLONE: ZC14279

(xi) SEQUENCE DESCRIPTION: SEQ ID NO:32:

CTGTGATTTC ATGGTCGTAG TCTTCAGTGG TGCTGAAATA CTTGCCTCCT           50

(2) INFORMATION FOR SEQ ID NO:33:

(i) SEQUENCE CHARACTERISTICS:
          (A) LENGTH: 139 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:33:

AGCATTGCTG CTAAAGAAGA AGGTGTAAGC TTGGACAAGA GAGATTACAA GGACGATGAT    60

GACAAGGGTG GTGGGAAGAT GTATGGCCCT GGAGGAGGCA AGTATTTCAG CACCACTGAA   120

GACTACGACC ATGAAATCA                                                139

(2) INFORMATION FOR SEQ ID NO:34:

(i) SEQUENCE CHARACTERISTICS:
          (A) LENGTH: 68 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (B) CLONE: ZC14346

(xi) SEQUENCE DESCRIPTION: SEQ ID NO:34:

CAGTTAATCT CACATACTCA GCAAACTCAC CCGTGGGTCG CTAGGAATTC TAGTATTCTA    60

GGGCTGCC                                                            68

(2) INFORMATION FOR SEQ ID NO:35:

(i) SEQUENCE CHARACTERISTICS:
          (A) LENGTH: 60 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (B) CLONE: ZC14218

(xi) SEQUENCE DESCRIPTION: SEQ ID NO:35:

TGGCAAACTC TCAAAAATTA TAAAAATATC CAAACAGGCA GCCCTAGAAT ACTAGAATTC    60

(2) INFORMATION FOR SEQ ID NO:36:

(i) SEQUENCE CHARACTERISTICS:
          (A) LENGTH: 51 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (B) CLONE: ZC14278

(xi) SEQUENCE DESCRIPTION: SEQ ID NO:36:

ACTAGAGGAG CCGACCACTG AGCCACCAGT TAATCTCACA TACTCAGCAA A            51

(2) INFORMATION FOR SEQ ID NO:37:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC13734

(xi) SEQUENCE DESCRIPTION: SEQ ID NO:37:

```
ATCATAGAAG AGAAAAACAT TAGTTGGCAA ACTCTCAAAA ATTATAAAAA TA        52
```

(2) INFORMATION FOR SEQ ID NO:38:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

```
ACTAGAGGAG CCGACCACTG AGCCACCAGT TAATCTCACA TACTCAGCAA ACTCACCCGT        60

GGGTCGCTAG GAATTCTAGT ATTCTAGGGC TGCCTGTTTG GATATTTTTA TAATTTTTGA       120

GAGTTTGCCA ACTAATGTTT TTCTCTTCTA TGAT                                  154
```